United States Patent [19]

Webb et al.

[11] Patent Number: 5,371,072

[45] Date of Patent: Dec. 6, 1994

[54] ASP-PRO-ARG α-KETO-AMIDE ENZYME INHIBITORS

[75] Inventors: Thomas R. Webb; Todd A. Miller, both of Encinitas; George P. Vlasuk, Carlsbad, all of Calif.

[73] Assignee: Corvas International, Inc., San Diego, Calif.

[21] Appl. No.: 962,301

[22] Filed: Oct. 16, 1992

[51] Int. Cl.$^5$ .................. A61K 37/00; A61K 37/02; C07K 5/08

[52] U.S. Cl. ..................... 514/18; 514/822; 530/331

[58] Field of Search ............ 514/18, 822; 530/331

[56]  References Cited

U.S. PATENT DOCUMENTS

| | | | |
|---|---|---|---|
| 3,966,701 | 6/1976 | Dorman et al. | 530/331 |
| 4,161,522 | 7/1979 | Hamburger | 514/15 |
| 4,171,299 | 10/1979 | Hamburger | 530/329 |
| 4,478,745 | 10/1984 | Bojusz et al. | 530/331 |
| 5,221,752 | 6/1993 | Someno et al. | 548/540 |

*Primary Examiner*—Douglas W. Robinson
*Assistant Examiner*—Jon P. Weber
*Attorney, Agent, or Firm*—Lyon & Lyon

[57]  ABSTRACT

Asp-Pro-Arg alpha-keto-amide derivatives, and their pharmaceutically acceptable salts and compositions, for use as antithrombotic agents in mammals are disclosed. The method of use of these inhibitor compounds for treatment or prevention of conditions of abnormal thrombus formation in mammals is also disclosed. Further disclosed are alpha-hydroxy amide compounds used as intermediates in the preparation of the keto-amide compounds.

35 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 4 AMINO ACIDS
        ( B ) TYPE: AMINO ACID
        ( D ) TOPOLOGY: LINEAR ( i i ) MOLECULE TYPE: PEPTIDE ( x i ) SEQUENCE DESCRIPTION: SEQ ID NO: 1:

Gly Val Arg Gly
1

( 2 ) INFORMATION FOR SEQ ID NO: 2:

( i ) SEQUENCE CHARACTERISTICS:
        ( A ) LENGTH: 4 AMINO ACIDS
        ( B ) TYPE: AMINO ACID
        ( D ) TOPOLOGY: LINEAR ( i i ) MOLECULE TYPE: PEPTIDE ( x i ) SEQUENCE DESCRIPTION: SEQ ID NO: 2:

Ser Ala Arg Gly
1

( 2 ) INFORMATION FOR SEQ ID NO: 3:

( i ) SEQUENCE CHARACTERISTICS:
        ( A ) LENGTH: 3 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            1Xaa is D- Phe and 3Xaa is Argininal ( x i ) SEQUENCE DESCRIPTION: SEQ ID NO: 3:

Xaa  Pro  Xaa
1

( 2 ) INFORMATION FOR SEQ ID NO: 4:

( i ) SEQUENCE CHARACTERISTICS:
        ( A ) LENGTH: 3 AMINO ACIDS
        ( B ) TYPE: AMINO ACID
        ( D ) TOPOLOGY: LINEAR ( i i ) MOLECULE TYPE: PEPTIDE ( i x ) FEATURE:
        ( D ) OTHER INFORMATION:
            1Xaa is (D- Phe) and 3Xaa is borated Arg ( x i ) SEQUENCE DESCRIPTION: SEQ ID NO: 4:

Xaa  Pro  Xaa
1

ASP-PRO-ARG α-KETO-AMIDE ENZYME INHIBITORS

FIELD OF THE INVENTION

The present invention relates in one aspect to novel compounds, their pharmaceutically acceptable salts and pharmaceutically acceptable compositions thereof which are useful as potent and specific inhibitors of blood coagulation in mammals. In another aspect, the invention relates to a methods of using these inhibitors as therapeutic agents for disease states characterized by disorders of the blood coagulation process. In yet another aspect, the invention relates to intermediate compounds for the preparation of the inhibitors.

BACKGROUND AND INTRODUCTION TO THE INVENTION

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33:479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation. These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways. The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M. D. and C. D. Forbes. M. D. edit. 1984).

This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

Proteolytic activation of zymogen factor X to its catalytically active form, factor Xa, results in the liberation of a 52 amino acid activation peptide from the amino-terminus of the heavy chain subunit. The intrinsic activation reaction is catalyzed by factor IXa in a macromolecular complex with the non-enzymatic co-factor, factor VIIIa. Factor Xa formation via the extrinsic pathway is catalyzed by the catalytic complex of factor VIIa and tissue factor. Both of these reactions must occur on an appropriate phospholipid surface in the presence of calcium ions. The active product formed following either intrinsic or extrinsic activation of factor X is a-factor Xa. A second proteolytic cleavage which is thought to be autocatalytic, results in the formation of β-factor Xa following the release of a 14 amino acid peptide from the carboxy-terminus of the heavy chain. Both forms of the activated molecule have the same catalytic activity as measured by their ability to promote coagulation in plasma or hydrolyze a peptidyl chromogenic substrate.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76:1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383– 1391 (1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105:58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405:349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84:18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77:2641 (1991). This positive feedback process results in the local generation of large concentrations of thrombin within the vicinity of the thrombus which supports further thrombus growth and extension. Mann, K. G. et al., Blood, 77: 2641 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27:769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235:1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72:131 (1975). The direct interaction of thrombin with vascular smooth muscle also results in vasoconstriction. Walz, D. A. et al., Proc. Soc. Expl. Biol. Med., 180:518 (1985). Thrombin acts as a direct secretagogue inducing the release of a number of bioactive substances from vascular endothelial cells including tissue plasminogen activator. Levin, E. G. et al., Thromb. Haemost., 56:115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet α-granules following thrombin-induced activation. Ross, R., N. Engl. J. Med., 314:408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. There is currently no effective therapy for the treatment or prevention of acute arterial thrombosis or rethrombosis since heparin, the most widely used clinical anticoagulant administered i.v., has not been shown to be universally effective in this setting. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of factor Xa as the catalyst for the penultimate step in the blood coagulation cascade which is the formation of the serine protease thrombin.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

|  | P3 | P2 | P1 | P1' |  |
|---|---|---|---|---|---|
|  | —Gly— | Val— | Arg/ | Gly | Fibrinogen Aα Chain |
|  | —Ser— | Ala— | Arg/ | Gly | Fibrinogen Bβ Chain |

Peptidyl derivatives having an uncharged residue in the P3 position which is believed to bind to the active site of thrombin and thereby inhibit the conversion of fibrinogen to fibrin and cellular activation have been reported. Additionally, these derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25:277 (1984), Bajusz, S. et al, J. Med. Chem., 33:1729 (1990) and Bajusz, S. et al., Int. J. Peptide Protein Res. 12: 217 (1970); Kettner, C. and Shaw, E., Methods Enzymol., 80:826 (1987); Kettner, C. et al., EP 293,881 (published Dec. 7, 1988); Kettner, C., et al., J. Biol. Chem., 265:18209 (1990). These molecules have been reported to be potent anticoagulants in the prevention of platelet-rich arterial thrombosis. Kelly, A. B. et al., Thromb. Haemostas., 65:736 at abstract 257 (1991).

Peptidyl compounds which are said to be active site inhibitors of thrombin but which are said to differ in structure to those containing a uncharged amino acid in the P3 recognition subsite have been reported. The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101:440 (1981). Argatroban has been reported to be a potent antithrombotic agent in several experimental models of acute arterial thrombosis. Jang, I. K. et al., in both Circulation, 81:219 (1990) and Circ. Res., 67:1552 (1990).

Peptidyl compounds which are said to be inhibitors of thrombin and whose mode of action is thought to be by binding to the active site and another site on the enzyme have been reported. Hirudin and its various peptidyl derivatives have been reported to inhibit both conversion of fibrinogen to fibrin and platelet activation by binding to either the active site and exo site, or exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64:344 (1990). It is reported to inhibit thrombin by binding to both its anion-binding exosite and to its catalytic active site which are distinct and physically distant from each other. Rydel, supra. Hirudin has been reported to be a potent antithrombotic agent in vitro. Markwardt, F. et al., Pharmazie, 43:202 (1988); Kelly, A. B. et al., Blood, 77:1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84:232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264:8692 (1989); Naski, M. C. et al., J. Biol. Chem., 265:13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65:830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, supra. Hirugen also is reported to block thrombin-mediated platelet aggregation. Jakubowski, J. A. and Maraganore, J. M., Blood, 75:399 (1990).

Hirulog has been reported to be a synthetic chimeric molecule comprised of a hirugen-like sequence linked by a glycine-spacer region to the peptide, D-phenylalanyl-prolyl-arginine which is based on a preferred substrate recognition site for thrombin. The hirugen-like sequence is said to be linked to this peptide through the C-terminal end of the peptide. Maraganone, J. M. et al., Biochemistry, 29:7095 (1990). Hirulog has been reported to be an effective antithrombotic agent in preventing both fibrin-rich and platelet-rich thrombosis. Maraganone, J. M. et al., Thromb. Haemòstas., 65:651 at abstract 17 (1991).

Cyclotheonamide A and B, isolated from the marine sponge, Theonella, a genus of marine sponges, have been reported to be inhibitors of thrombin with an $IC_{50}$ of 0.076 μg/mL. Structurally, they have been characterized as cyclic peptides containing an α-keto amide moiety. Fusetani et al., J. Am. Chem. Soc. 112: 7053–7054 (1991) and Hagihara et al., J. Am. Chem. Soc, 114: 6570–6571 (1992). It has been proposed that the α-keto group of the cyclotheonamides may function as an electrophilic mimic of the Arg-X scissile amide bond of the thrombin substrates. Hagihara et al., Id. at 6570. The partial synthesis of cyclotheonamide A and the total synthesis of cyclotheonamide B have been reported. wipf et al., Tetrahedron Lett., 33:4275–4278 (1992) and Hagihara et al., J. Am. Chem. Soc, 114: 6570–6571 (1992).

α-Keto ester derivatives of N-protected amino acids and peptides have been reported as inhibitors of serine proteases, as neutrophil elastase and cathepsin. G. Mehdi et al., Biochem. Biophys. Res. Commun., 166: 595–600 (1990) and Angelastro et al., J. Med. Chem., 33: 11–13 (1990).

Alpha keto-amide derivatives of amino acids and peptides have been reported to be inhibit proteases. For example, fluoro-substituted keto amide derivatives have been reported to be inhibitors of proteases. European Patent Application No. 275,101 (published Jul. 20, 1988). L-valyl-L-valyl-3-amino-2-oxovaleryl-D-leucyl-L-valine had been reported to be an inhibitor of prolyl endopeptidase. Nagai et al., J. Antibiotics, 44: 956–961 (1991). 3-Amino-2-oxo-4-phenylbutanoic acid amide has been reported to be an inhibitor of arginyl aminopeptidase (with inhibitor constant of 1.5 μM), cytosol aminopeptidase (with inhibitor constant of 1.0 μM) and microsomal aminopeptidase (with inhibitor constant of 2.5 μM). Ocain et al., J. Med. Chem., 35: 451–456 (1992). 2-Oxo-2-(pyrrolidin-2yl) acetyl derivatives have been reported to be inhibitors of prolyl endopeptidase. Someno et al., European Patent Application No. 468,339 (published Jan. 29, 1992). Certain alpha ketoamide derivatives of peptides have been reported to inhibit various serine and cysteine proteases. Powers J. C., International Application No. WO 92/12140 (published Jul. 23, 1992).

SUMMARY OF THE INVENTION

In one aspect, the present invention in one aspect is directed to novel compounds which are useful as antithrombic agents. These compounds have the structure:

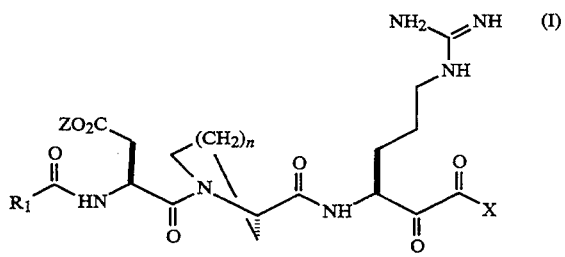

wherein $R_1$ is alkyl of about 1 to about 12 carbon atoms, alkenyl of about 3 to about 6 carbon atoms, aryl of about 6 to about 14 carbon atoms, aralkyl of about 6 to 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms;

Z is hydrogen, alkyl of about 1 to about 12 carbon atoms, alkenyl of about 3 to about 6 carbon atoms, aryl of about 6 to about 14 carbon atoms, aralkyl of about 6 to about 15 carbon atoms, or aralkenyl of about 8 to about 15 carbon atoms;

n is 0, 1, or 2; and

X is —N ($R_2$)—Y—Ar,

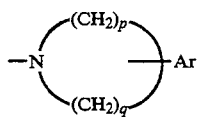

or —NH($R_6$), wherein $R_2$ is hydrogen, lower alkyl of about 1 to about 4 carbon atoms, or aryl of about 6 to about 14 carbon atoms; Ar is an aryl of about 6 to about 14 carbon atoms which is optionally substituted with 1 or 2 substituents each independently selected from a group consisting of amino, carboxy, carboxamide, fluoro, nitro, trifluoromethyl, lower alkyl of about 1 to about 4 carbon atoms, and lower alkoxy of about 1 to about 4 carbon atoms;

Y is —CH($R_3$)—, —CH($R_3$)—CH($R_4$)—, or —CH($R_3$)—CH($R_4$)—CH($R_5$)—, wherein $R_3$ is hydrogen, carboxy, carboxamide, alkylenehydroxy of about 1 to about 4 carbon atoms, lower alkyl of about 1 to about 4 carbon atoms, alkylenecarboxy of about 2 to about 5 carbon atoms, alkylenecarboxamide of about 2 to about 5 carbon atoms, or aryl of about 6 to about 14 carbon atoms; $R_4$ is hydrogen, lower alkyl of about 1 to about 4 carbon atoms, or aryl of about 6 to about 14 carbon atoms; and $R_5$ is hydrogen, lower alkyl of about 1 to about 4 carbon atoms, or aryl of about 6 to about 14 carbon atoms, p and q are independently selected integers from 1 to 5 and the sum of p+q is 4 to 8; and $R_6$ is naphthyl, 1,2,3,4-tetrahydronaphthyl, (1,2,3,4-tetrahydronaphthyl)methylene, or indanyl; provided that no more than one $R_3$, $R_4$, or $R_5$ is aryl; and pharmaceutically acceptable salts thereof.

Preferred $R_1$ groups include branched alkyl groups; particularly preferred are $R_1$ groups which are branched at the 2- or α-position.

Especially preferred groups for $R_1$ include 2,2-dimethylethyloxy, 2,2-dimethylpropyl, 3-methylbutyl, or 1-propylbutyl; for Z hydrogen and indan-5-yl; and for X 2-phenylethylamine or 3-phenylpropylamine. Preferably, n is 1.

Preferred are compounds where X is —N($R_2$)—CH($R_3$)—CH($R_4$) —Ar or —N($R_2$)—CH ($R_3$)—CH ($R_4$)—CH($R_5$ )—Ar; particularly preferred are such X groups wherein all of $R_2$, $R_3$, $R_4$ and $R_5$ are hydrogen.

Also preferred are compounds wherein X is —NH($R_2$)CH($R_2$)—CH($R_3$)—Ar wherein $R_2$ is hydrogen and $R_3$ is phenyl; particularly preferred are such X groups wherein Ar is also phenyl.

Another preferred group of compounds include those wherein X is —NH($R_6$). Particularly preferred $R_6$ groups include 2-naphthyl, 2-(1,2,3,4-tetrahydronaphthyl)methylene and indane-2-yl.

The compounds of the instant invention can be divided into parts as shown in the following formula Ia:

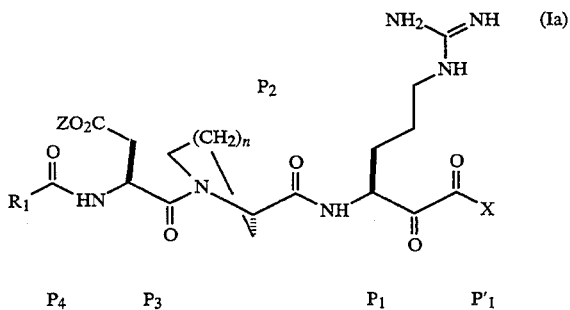

wherein $R_1$, n and X are as defined in connection with formula I. In formula Ia, $P_1$ corresponds to the arginine residue, $P_2$ corresponds to the cyclic amino acid residue, and $P_3$ corresponds to the aspartic acid residue or aspartic acid ester residue. In a particular compound, the $R_1$ and X groups for $P_4$ and $P_1'$ respectively are selected depending on the specific enzyme to be selectively inhibited.

Among other factors, the present invention is based on our surprising finding that the compounds of formula I which include at the $P_3$ position an aspartic acid residue or suitable ester derivative of aspartic acid are highly active inhibitors of coagulation. Certain of these compounds exhibit $IC_{50}$'s in an assay of thrombin inhibition of less than 10 nm. (See Example A). Suitable ester derivatives of aspartic acid include those that can be cleaved in vivo to yield the corresponding aspartic acid derivative. Such esters are believed to exhibit improved bioavailability and to have a longer half life in the circulation. The preferred compounds of formula I have $R_1$ groups which preferably comprise branched hydrophobic groups which have been selected so as to enhance potency and/or selectivity of these compounds.

In another aspect, the present invention is directed to a pharmaceutical composition for treating coagulation disorders which comprises a pharmaceutically acceptable carrier and a therapeutically effective amount of a compound of the present invention.

In yet another aspect, the present invention is directed to methods of preventing or treating in a mammal a condition characterized by abnormal thrombus formation.

One aspect of the present invention allows the stereoselective synthesis which yields the optically pure arginine ketoamides of formula I. Thus, in another aspect, the present invention is directed to intermediates useful for the preparation of the compounds of the present invention. These intermediates have the structure:

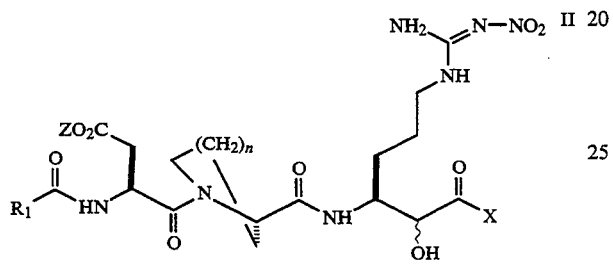

wherein $R_1$ is alkyl of about 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms;

Z in hydrogen, alkyl of about 1 to about 12 carbon atoms, alkenyl of about 3 to about 6 carbon atoms, aryl of about 6 to about 14 carbon atoms, aralkyl of about 6 to about 15 carbon atoms, or aralkenyl of about 8 to about 15 carbon atoms;

n is 0, 1, or 2; and

X is —N($R_2$)—Y—Ar,

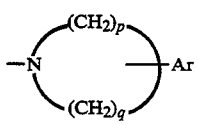

or —NH($R_6$), wherein $R_2$ is hydrogen, lower alkyl of about 1 to about 4 carbon atoms, or aryl of about 6 to about 14 carbon atoms; Ar is an aryl of about 6 to about 14 carbon atoms which is optionally substituted with 1 or 2 substituents each independently selected from a group consisting of amino, carboxy, carboxamide, fluoro, nitro, trifluoromethyl, lower alkyl of about 1 to about 4 carbon atoms, and lower alkoxy of about 1 to about 4 carbon atoms; Y is —CH($R_3$)—, —CH($R_3$)—CH($R_4$)—, or —CH($R_3$)—CH($R_4$)—CH($R_5$)—, wherein $R_3$ is hydrogen, carboxy, carboxamide, alkylenehydroxy of about 1 to about 4 carbon atoms, lower alkyl of about 1 to about 4 carbon atoms, alkylenecarboxy of about 2 to about 5 carbon atoms, alkylenecarboxamide of about 2 to about 5 carbon atoms, or aryl of about 6 to about 14 carbon atoms; $R_4$ is hydrogen, lower alkyl of about 1 to about 4 carbon atoms, or aryl of about 6 to about 14 carbon atoms; and $R_5$ is hydrogen, lower alkyl of about 1 to about 4 carbon atoms, or aryl of about 6 to about 14 carbon atoms; p and q are independently selected integers from 1 to 5 and the sum of p+q is 4 to 8; and $R_6$ is naphthyl, 1,2,3,4-tetrahydronaphthyl, (1,2,3,4-tetrahydronaphthyl)methylene, or indanyl; provided that no more than one $R_3$, $R_4$, or $R_5$ is aryl.

Preferred $R_1$ groups include branched-chain alkyl groups; particularly preferred are $R_1$ groups which are branched at the 2- or α-position.

Groups especially preferred for R1 include 2,2-dimethylethyloxy, 3-methylbutyl, 2,2-dimethylpropyl, or 1-propylbutyl. Especially preferred compounds include those where Z is benzyl; n is 1; and x are 2-phenylethylamine or 3-phenylpropylamine.

Definitions

In accordance with the present invention and as used herein, the following terms are defined with the following meanings, unless explicitly stated otherwise.

The term "alkyl" refers to saturated aliphatic groups including straight-chain, branched-chain and cyclic groups.

The term "alkenyl" refers to unsaturated hydrocarbyl groups which contain at least one carbon-carbon double bond and includes straight-chain, branched-chain and cyclic groups The term "alkylene" refers to a divalent straight chain or branched chain saturated aliphatic radical.

The term "aryl" refers to aromatic groups which have at least one ring having a conjugated pi electron system and includes carbocyclic aryl, heterocyclic aryl and biaryl groups, all of which may be optionally substituted.

The term "aralkyl" refers to an alkyl group substituted with an aryl group. Suitable aralkyl groups include benzyl, picolyl, and the like, all of which may be optionally substituted.

The term "aralkenyl" refers to an alkenyl group substituted with an aryl group. Suitable aralkenyl groups include styrenyl and the like, all of which may be optionally substituted.

The term "alkoxy" refers to the group —OR wherein R is alkyl.

The term "alkenyloxy" refers to the group —OR wherein R is alkenyl.

The term "aryloxy" refers to the group —OR wherein R is aryl.

The term "aralkyloxy" refers to the group —OR wherein R is aralkyl.

The term "methylene" refers to —$CH_2$—.

The term "alkylenecarboxy" refers to the group —alk—COOH where alk is alkylene.

The term "carboxamide" refers to the group —C(O)$NH_2$.

The term "alkylenecarboxamide" refers to the group —alk—C(O)$NH_2$ where alk is alkylene.

The term "alkylenehydroxy" refers to the group —alk—OH wherein alk is alkylene.

In addition, the following abbreviations stand for the following:

"Bn" refers to benzyl.

"Boc" refers to t-butoxycarbonyl.

"Boc₂O " refers di-t-butyldicarbonate.

"BocAsp$^{Bn}$—OH" refers to N-Boc-L-aspartic acid-($\beta$-benzyl ester).

"BocPro—OH" refers to N-Boc-L-proline.

"BOP" refers to benzotriazol-1-yloxy-tris-(dimethylamino)-phosphonium-hexafluorophosphate.

"Brine" means an aqueous saturated solution of sodium chloride.

"TFA" refers to trifluoroacetic acid.

BRIEF DESCRIPTION OF THE DRAWINGS

In FIG. 1, i represents potassium cyanide, potassium bicarbonate, water; ii represents HCl/water/dioxane; iii represents dry HCl/methanol; iv represents Boc-2O/THF/NaHCO₃/H₂O/; v represents lithium hydroxide/methanol/water; vi represents Dowex-50 acid form; vii represents X-NH₂/BOP/DMF where X is as defined in connection with formula I; viii represents TFA/methylene chloride; ix represents Boc-Pro-OH/BOP/DMF; x represents Boc-Asp$^{Bn}$-OH/BOP/DMF; xi represents modified Moffatt conditions; and xii represents either H₂/Pd on carbon or HF/anisole.

DETAILED DESCRIPTION OF THE INVENTION

Preferred Compounds

Figure 1:
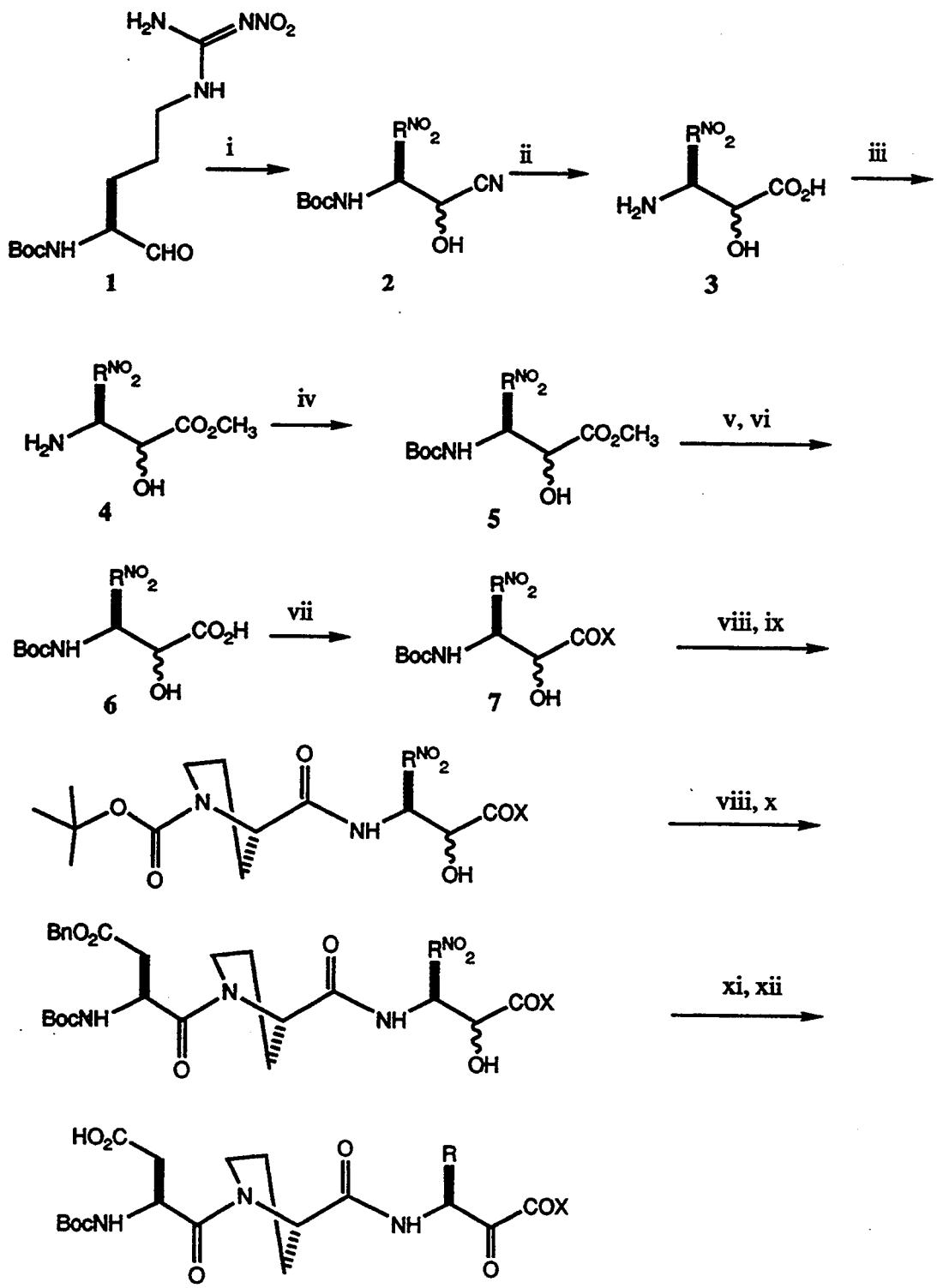
FIG. 1 depicts a reaction scheme describing a process for synthesis of the compounds of the present invention.

Preferred compounds of the present invention are those represented by formula I:

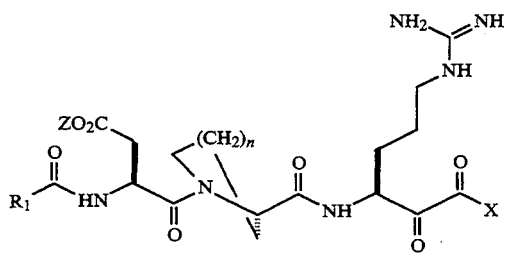

wherein

R₁ is alkyl of about 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms;

z is hydrogen, alkyl of about 1 to about 12 carbon atoms, alkenyl of about 3 to about 6 carbon atoms, aryl of about 6 to about 14 carbon atoms, aralkyl of about 6 to about 15 carbon atoms, or aralkenyl of about 8 to about 15 carbon atoms;

n is 0, 1, or 2; and x is —N(R₂)—Y—Ar,

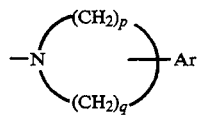

or —NH (R₆) , wherein R₂ is hydrogen, lower alkyl of about 1 to about 4 carbon atoms, or aryl of about 6 to about 14 carbon atoms; Ar is an aryl of about 6 to about 14 carbon atoms which is optionally substituted with 1 or 2 substituents each independently selected from a group consisting of amino, carboxy, carboxamide, fluoro, nitro, trifluoromethyl, lower alkyl of about 1 to about 4 carbon atoms, and lower alkoxy of about 1 to about 4 carbon atoms; and Y is —CH(R₃)—, —CH(R₃)—CH(R₄)—, or —CH(R₃)—CH(R₄)—CH(R₅)—, wherein R₃ is hydrogen, carboxy, carboxamide, alkylenehydroxy of about 1 to 4 carbon atoms, lower alkyl of about 1 to about 4 carbon atoms, alkylenecarboxy of about 2 to about 5 carbon atoms, alkylenecarboxamide of about 2 to about 5 carbon atoms, or aryl of about 6 to about 14 carbon atoms; R₄ is hydrogen, lower alkyl of about 1 to about 4 carbon atoms, or aryl of about 6 to about 14 carbon atoms; and R5 is hydrogen, lower alkyl of about 1 to about 4 carbon atoms, or aryl of about 6 to about 14 carbon atoms; p and q are independently selected integers from 1 to 5 and the sum of p+q is 4 to 8; and R₆ is naphthyl, 1,2,3,4-tetrahydronaphthyl, (1,2,3,4-tetrahydronaphthyl)methylene, or indanyl; provided that no more than one R₃, R₄, or R₅ is aryl of about 6 to about 14 carbon atoms.

Preferred compounds include those wherein R₁ is a linear or branched alkyl of about 1 to about 12 carbons. Suitable alkyl groups include methyl, ethyl, 1,1-dimethylethyl, propyl, 2-methylpropyl, 2,2-dimethylpropyl, butyl, 3-methylbutyl, 1-propylbutyl, pentyl, hexyl, cyclopentyl, cyclopentylmethyl, cyclohexyl, cyclohexylmethyl, adamantyl, adamantylmethyl, 2-propenyl, 3-butenyl, 1-pentenyl, 2-pentenyl, 5-hexenyl, 2-cyclopentenyl, phenyl, phenylmethyl, diphenylmethyl, biphenyl, biphenylmethyl, naphthyl, naphthylmethyl, α-phenylmethylphenyl, 2-phenylethylene, 1,1-dimethylethyloxy, 2-methylpropyloxy, 2,2-dimethylpropyloxy, cyclopentyloxy, cyclopentylmethyloxy, cyclohexyloxy, cyclohexylmethyloxy, adamantyloxy, adamantylmethoxy, phenoxy, benzyloxy, biphenylmethyloxy, naphtholoxy or naphthylmethyloxy. Especially preferred R₁ groups are branched alkyl groups of about 1 to 12 carbons and include 2,2-dimethylethyloxy, 2,2-dimethylpropyl, 3-methylbutyl, and 1-propylbutyl. One particularly preferred class of R₁ groups are branched alkyl groups branched at the 2- or α-position.

Preferred are compounds where Z is hydrogen or indan-5-yl.

Preferred are compounds wherein n is 1 or 2; especially preferred are compounds where n is 1.

Preferred are compounds where X is —N(R₂)—Y—Ar, wherein R₂ is hydrogen or lower alkyl of about 1 to about 4 carbon atoms; Y is —CH(R₃ )—, —CH(R₃ )—CH (R₄)—, or —CH(R₃)—CH(R₄)—CH(R₅)—; and Ar is aryl of about 6 to about 14 carbon atoms. Especially preferred as R₂ is hydrogen. Especially preferred Y groups include —CH(phenyl)—, —CH(CO₂H)—CH₂ —, —CH(CH₂—OH)—CH₂—, —CH₂—CH₂—, and —CH₂—CH₂—CH₂—. Especially preferred Ar groups include phenyl, naphthyl, biphenyl, α-phenylmethylphenyl, 2-thienyl, 2-pyrrolyl, and 2-furyl. Also preferred are those compounds wherein X is —NH(R₆), wherein R₆ is naphthyl, 1,2,3,4-tetrahydronaphthyl, (1,2,3,4-tetrahydronaphthyl) methylene, or indanyl. Especially preferred are compounds wherein R₆ is 2-naphthyl, 1-naphthyl, 2- (1,2,3,4-tetrahydronaphthyl), 2- (1,2,3,4-tetrahydronaphthyl)-methylene or 2-indanyl.

Especially preferred compounds of the present invention include:

both forms being considered as being within the scope of the present invention. These salts include acid addition salts, for example, salts of hydrochloric acid, hydrobromic acid, acetic acid, benzene sulfonic acid and

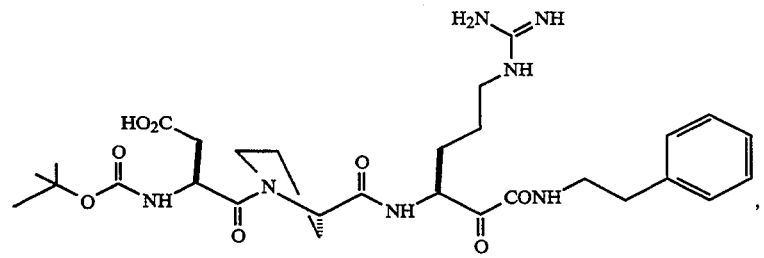

[1]

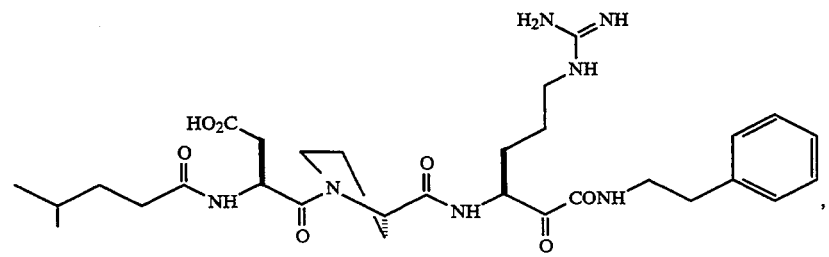

[2]

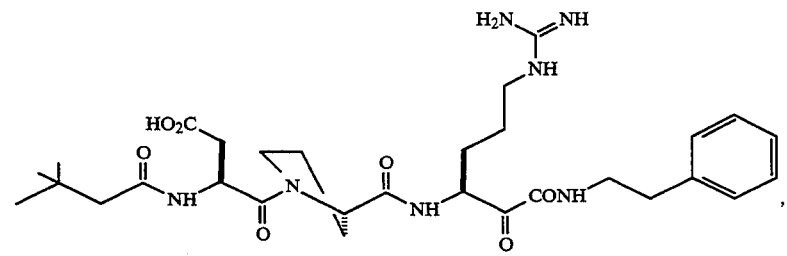

[3]

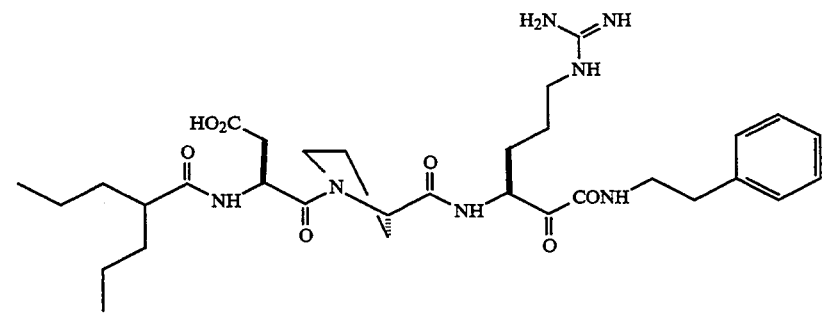

[4]

and

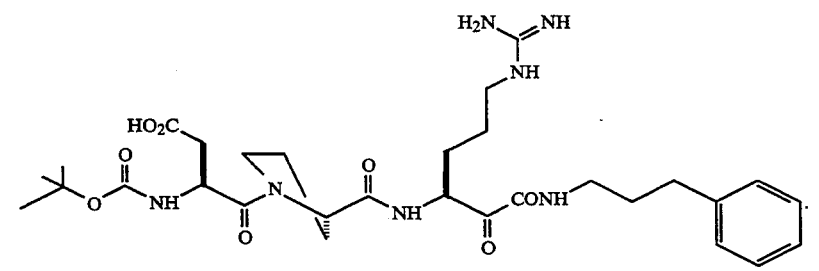

[5]

According to another aspect, the present invention is directed to pharmaceutically acceptable salts of the compounds of formula I. "Pharmaceutically acceptable salt" includes within its definition salts of the compounds of the present invention derived from the combination of a such compounds and an organic or inorganic acid. In practice, the use of the salt form amounts to use of the base form. The compounds of the present invention are useful in both free base and salt form, with other suitable acid addition salts.

In yet another aspect, the present invention is directed to compounds useful as intermediates for the preparation of compounds represented by formula I. These intermediates are represented by formula II:

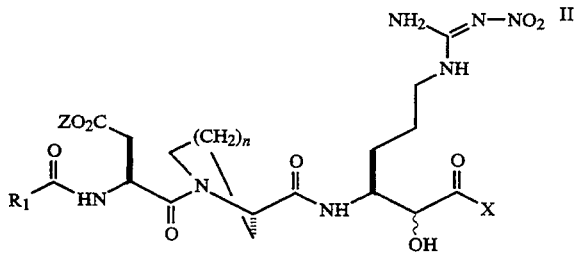

wherein Z, n, R$_1$, and X are defined as above in formula I.

In view of the above-noted preferred compounds, preferred intermediates include those wherein R$_1$ is a linear or branched alkyl of about 1 to about 12 carbons. Such alkyl groups include methyl, ethyl, 1,1-dimethylethyl, propyl, 2-methylpropyl, 2,2-dimethylpropyl, butyl, 3-methylbutyl, 1-propylbutyl, pentyl, hexyl, cyclopentyl, cyclopentylmethyl, cyclohexyl, cyclohexylmethyl, adamantyl, adamantylmethyl, 2-propenyl, 3-butenyl, 1-pentenyl, 2-pentenyl, 5-hexenyl, 2-cyclopentenyl, phenyl, phenylmethyl, diphenylmethyl, biphenyl, biphenylmethyl, naphthyl, naphthylmethyl, α-phenylmethylphenyl, 2-phenylethylene, 1,1-dimethylethyloxy, 2-methylpropyloxy, 2,2-dimethylpropyloxy, cyclopentyloxy, cyclopentylmethyloxy, cyclohexyloxy, cyclohexylmethyloxy, adamantyloxy, adamantylmethoxy, phenoxy, benzyloxy, biphenylmethyloxy, naphtholoxy or naphthylmethyloxy. Especially preferred are branched alkyls of about 1 to 12 carbons such as 2,2-dimethylethyloxy, 2,2-dimethylpropyl, 3-methylbutyl, and 1-propylbutyl.

Preferred are intermediates where Z is aralkyl of about 6 to about 15 carbon atoms, or aralkenyl of about 8 to about 15 carbon atoms. Especially preferred are intermediates where Z is benzyl.

Preferred are intermediates where n is 1 or 2, with 1 being especially preferred as n.

One preferred class of intermediates include those where X is —N(R$_2$)—Y—Ar, wherein R$_2$ is H or lower alkyl of about 1 to about 4 carbon atoms; Y is —CH(R$_3$)—, —CH(R$_3$)—CH(R$_4$)—, or —CH(R$_3$)—CH(R$_4$)—CH(R$_5$)—; and Ar is an aryl of about 6 to about 14 carbon atoms. Especially preferred as R$_2$ is hydrogen. Especially preferred Y groups include: —CH(phenyl)—, —CH(CO$_2$H)—CH$_2$—, —CH(CH$_2$—OH)—CH$_2$—, —CH$_2$—CH$_2$—, and —CH$_2$—CH$_2$—CH$_2$—. Especially preferred Ar groups include: phenyl, naphthyl, biphenyl, α-phenylmethylphenyl, 2-thienyl, 2-pyrrolyl, and 2- furyl.

Another preferred group of intermediates are those compounds, wherein X is —NH(R$_6$), wherein R$_6$ is naphthyl, 1,2,3,4-tetrahydronaphthyl, (1,2,3,4-tetrahydronaphthyl)methylene, or indanyl. Especially preferred R$_6$ groups include 2-naphthyl, 1-naphthyl, 2(1,2,3,4-tetrahydronaphthyl), 2- (1,2,3,4-tetrahydronaphthyl)methylene, and 2-indanyl.

Especially preferred intermediates include:

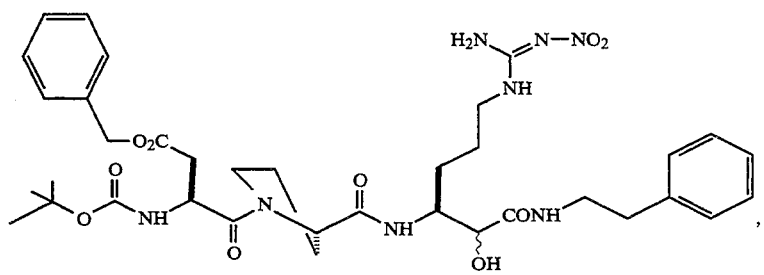

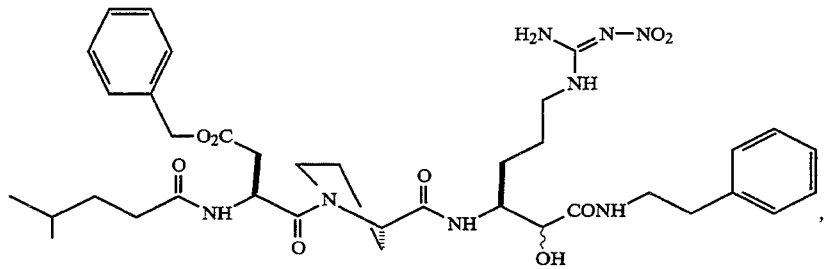

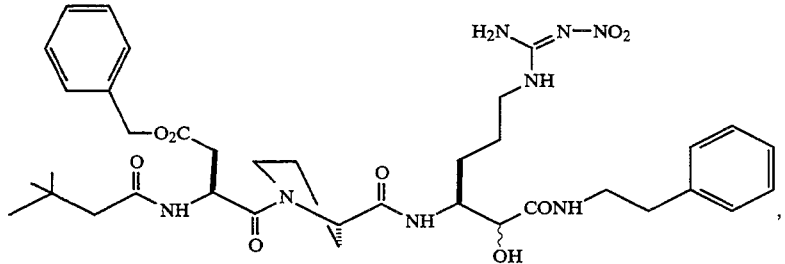

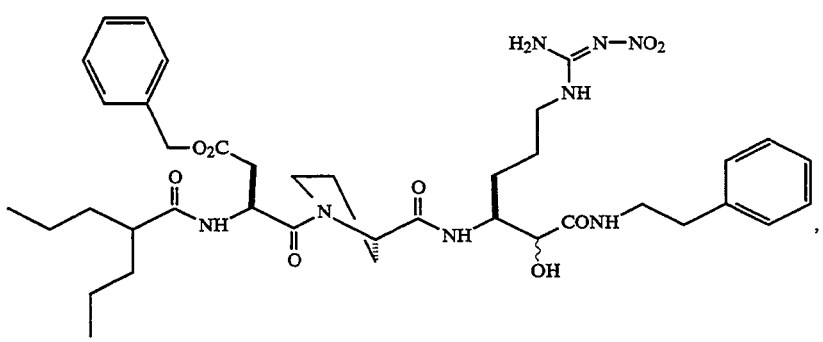

[9]

and

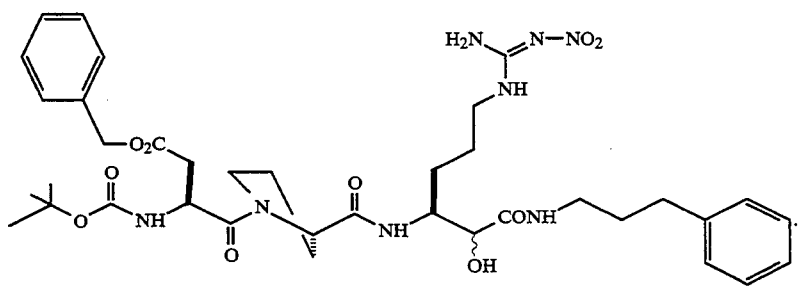

[10]

Preparation of Preferred Compounds

The preferred compounds of formula I may be conveniently prepared by liquid phase methods.

One method of synthesizing the compounds of formula I comprises converting the α-amino protected amino acid to an "activated" derivative wherein its carboxyl group is rendered more susceptible to reaction with the free N-terminal α-amino group of the target amino acid or peptide having an associated α-keto amide functionality. For example, the free carboxyl of the α-amino protected (N-protected) amino acid can be converted to a mixed anhydride by reaction of a N-protected amino acid with ethyl choloroformate, pivaloyl chloride or like acid chlorides. Alternatively, the carboxyl of the α-amino protected amino acid can be converted to an active ester such as a 2,4,5-trichloropheyl ester, a pentachlorophenol ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents are disclosed in E. Gross & J. Meinenhofer, The Peptides: Analysis, Structure, Biology, Vol. I: Major Methods of Peptide Bond Formation (Academic Press, New York, 1979).

The α-amino group of the target amino acid or peptide having an associated α-keto amide functionality employed in the synthesis of the compounds of the present invention is selectively de-protected during the coupling reaction to prevent side reactions involving the reactive, unprotected, side chain functionalities. In addition, reactive side-chain functional groups (e.g., amino, carboxyl, guanidinyl, hydroxyl, and sulfhydryl) must also be protected with suitable protecting groups to prevent chemical reaction of those groups from occurring during both the initial and subsequent coupling steps. Suitable protecting groups, known in the art, are described in E. Gross & J. Meienhofer, The Peptides: Analysis, Structure, Biology, Vol. 3: Protection of Functional Groups in Peptide Synthesis (Academic Press, New York, 1981).

In selecting suitable α-amino and reactive side-chain protecting groups to be used during synthesis of the compounds of formula I, the following considerations may be determinative. An α-amino protecting group should: (a) render the α-amino function inert (i.e., nonreactive) under the conditions employed in the coupling reaction, (b) be readily removable after the coupling reaction under conditions that will not remove side-chain protecting groups and will not alter the structure of the peptide fragment, and (c) eliminate the possibility of racemization upon activation immediately prior to coupling. An amino acid side-chain protecting group should: (a) render the protected side chain functional group inert under the conditions employed in the coupling reaction, (b) be stable under the conditions employed in removing the α-amino protecting group, and (c) be readily removable upon completion of the desired peptide under reaction conditions that will not alter the structure of the peptide chain.

It will be apparent to those skilled in the art that the protecting groups known to be useful for liquid phase peptide synthesis may vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl, t-amyloxycarbonyl, adamantyl-oxycarbonyl, and p-methoxybenxyloxycarbonyl are less labile and require moderately strong acids, such as trifluoroacetic, hydrochloric, or boron trifluoride in acetic acid, for their removal. Still other protecting groups, such as benxyloxycarbonyl, halobenxyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal.

Examples of amino acid protecting groups which are conventionally used include the following:

(1) For an α-amino group: (a) aromatic urethane-type protecting groups, such as fluorenylmethyloxycarbonyl (FMOC); (b) aliphatic urethane-type protecting groups, such as t-butyloxycarbonyl, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclo-pentyloxycarbonyl, adamantyloxycarbonyl, and cyclohexyloxy-carbonyl; and (d) allyloxycarbonyl. Preferred (α-amino protecting groups include t-butyloxycarbonyl or fluorenylmethyloxycarbonyl.

(2) For the side chain amino group present in lysine: protecting groups include any of the groups mentioned above in (1) such as t-butyloxycarbonyl, p-chlorobenzyloxycarbonyl, etc.

(3) For the quanidino group of arginine: protecting groups preferably include nitro, carbobenzyloxy, or 2,2,5,7,8-pentamethylchroman-6-sulfonyl or 2,3,6-trimethyl-4-methoxyphenylsulfonyl.

(4) For the hydroxyl group of serine, threonine, or tyrosine: protecting groups include, for example, t-butyl; benzyl; substituted benzyl groups, such as p-methoxybenzyl, p-nitrobenzyl, p-chlorobenzyl, o-chlorobenzyl, and 2,6-dichlorobenzyl.

(5) For the carboxyl group of aspartic acid or glutamic acid: protecting groups include, for example, by esterification using groups such as t-butyl, indan-5-yl or preferably benzyl.

(6) For the imidazole nitrogen of hystidine: suitable protecting groups include the benzyloxymethyl group (7) For the phenolic hydroxyl group tyrosine: protecting groups such as tetrahydropyranyl, tert-butyl, trityl, benzyl, chlorobenzyl, 4-bromobenzyl, and 2,6-dichlorobenzly are suitably employed. The preferred protecting group is bromo-benzyloxycarbonyl.

(8) For the side chain sulfhydryl group of cysteine: trityl is preferably employed as a protecting group.

Starting materials used in the preparation of these compounds are readily available from commercial sources as Aldrich, Bachem BioScience Inc., Nova Biochemicals, and Sigma.

According to one suitable reaction scheme, the compounds of formula I are prepared according to the following protocol. The α-amino protecting group is removed from a t-butyloxycarbonyl-protected amino acid or peptide having an associated α-keto amide functionality, such as by using trifluoroacetic acid in methylene chloride or trifluoroacetic acid alone. The deprotection is carried out at a temperature of from about 0° C. to about ambient temperature. Other suitable cleaving reagents, for removal of specific α-amino protecting groups, such as HCl in dioxane, may be used.

After the α-amino protecting group is removed from the amino acid or peptide, the desired α-amino and side-chain protected amino acid is coupled to the α-amino deprotected amino acid or peptide. Additional α-amino and side chain protected amino acids are coupled in a stepwise manner in the desired order until the desired sequence has been completed. As an alternative to adding each amino acid separately during the synthesis, several amino acids may be coupled to one another to give a peptide fragment prior to their coupling to the target amino acid analog. After the coupling steps are complete, the product peptide analog is deprotected to give the compound of formula I. Selection of an appropriate coupling reagent is within the skill of the art. Particularly suitable coupling reagents include N,N'-dicyclohexylcarbodiimide, diisopropylcarbodiimide or BOP.

The compounds of the present invention, represented in formula I above, are synthesized by a preferred liquid phase method as depicted in FIG. 1 and described below using the intermediates represented by formula II above.

Step A: The aldehyde functionality of the protected arginine aldehyde 1 is chemically replaced with an α-hydroxyacetic acid group to give the protected α-hydroxycarboxylic acid analogue of arginine, 6. Examples 2 to 4 describe a series of reactions exemplifying how the aldehyde group may be converted to an α-hydroxyacetic acid group.

Step B: The newly-introduced carboxy group on intermediate 6 is coupled using BOP to any suitable substituted amine, exemplified by amines such as 2-phenylethylamine in Example 5 or 3-phenylpropylamine as in Example 18, or by a protected amino acid as in Example 25 to give the amide 7. A suitable amine will be any sufficiently reactive amine in which other reactive groups are protected.

Step C: Suitably protected amino acids or peptides or peptide analogs are coupled to 7 after its N-terminus is deprotected. Examples 6, 9, 14 and 16 describe reactions coupling various N-protected-aspartyl-(β-benzyl ester)prolyl derivatives to amide 7, to give derivatives containing the α-hydroxycarboxylic analogues of arginine, as exemplified by Examples 6, 9, 12, 15, and 19.

Step D: The α-hydroxygroup of the resulting derivatives is oxidized to a keto group under modified Moffatt conditions. Edwards et al., J. Am. Chem. Soc., 114: 1854 at 1861 (1992). This gives the corresponding α-ketoamide derivatives, which are examples of the intermediates of the present invention. Exemplars of these intermediates are the compounds of Examples 7, 10, 13, 16 and 20.

Step E: The protecting groups on the α-ketoamide derivatives is removed by means of catalytic hydrogenation ($H_2$/Pd on Carbon) or HF deprotection using HF/anisole to give the compounds of the present invention. Exemplars of these compounds are the compounds of Examples 8, 11, 14, 17 and 21.

Purification of the compounds of the present invention is typically achieved using conventional procedures such as preparative HPLC (including reversed phase HPLC) or other known chromatography, affinity chromatography (including monoclonal antibody columns) or countercurrent distribution.

Utility and Formulation

The present invention provides the novel compounds of formula I, their pharmaceutically acceptable salts and compositions prepared from them. These compounds and pharmaceutical compositions are useful as inhibitors of coagulation proteases, both in vitro and in vivo.

As discussed in the Background and Introduction to the Invention, the formation of thrombin catalyzed by factor Xa is the penultimate reaction in the coagulation cascade and is a reaction common to both the intrinsic and extrinsic coagulation pathways which terminate in the formation of a fibrin clot. Inhibitors of this and other activated coagulation factors would therefore inhibit fibrin deposition, thrombus formation and the consumption of coagulation proteins.

Inhibitors of activated coagulation proteases may be used as pharmacological agents for the treatment of thrombotic disorders including, myocardial infarction, unstable angina, disseminated intravascular coagulation and associated complications resulting from venous thrombosis. These inhibitors may used as adjunctive or conjunctive agents to prevent recurrent thrombosis following enzymatic thrombolysis and percutaneous transluminal angioplasty. In addition, specific inhibitors of factor Xa may be useful in the supression of metastatic migration of certain tumor types as described by Tuszynski, G. P. et. al., "Isolation and characterization of antistasin, an inhibitor of metastasis and coagulation", J. Biol. Chem., 262:9718–9723 (1987) and Brankamp, R. G. et. al., "Ghilantens: anticoagulants, antimetastatic proteins from the South American leech *Haementeria ghilianii*", *J. Lab Clin. Med.*, 115: 89–97 (1990).

In mammals, in vivo uses would include administration of these compounds and compositions as therapeutic agents to prevent the formation of fibrin clots in blood vessels resulting from the presence of activated coagulation proteases, to prevent abnormal thrombus formation resulting from thrombotic disorders, and to prevent or treat the recurrent thrombus formation resulting from chemical or mechanical intervention directed to clearing blocked vessels. Additionally, the compounds, their salts and various compositions derived therefrom may be useful as therapeutic agents for suppressing the metastatic migration of tumor types in mammals.

The in vitro inhibitory activity of the compounds of the present invention may be demonstrated using an enzyme inhibition assay. The test compound is dissolved in a suitable assay buffer to give a solution having a concentration of test compound under assay conditions in the range of from 0 to about 100 $\mu$M. The enzyme whose activity is to be assayed is added to a solution containing a specified concentration of the test compound. After an incubation period, synthetic substrate for the enzyme is added. The rate of substrate turnover is determined spectrophotometrically at particular substrate concentrations. This data is used to determine an inhibition constant, Ki, for the test compound. Example A demonstrates that the compounds of Examples 8, 17, and 21 are potent inhibitors of human $\alpha$-thrombin, having Ki's of 11, 1.5 and 5.5 nanomolar, respectively. These assay results demonstrate that the compounds of formula I are as inhibitors of thrombin in vitro.

The in vivo inhibitory activity of the compounds of formula I in a rat model of acute thrombosis was demonstrated. (See Example B). The test compound was dissolved in a suitable diluent to give a test solution. The test solution is injected into a rat and the antithrombotic effect was measured. Example B demonstrated that the compound of Example 8 possessed antithrombic efficacy in vivo in a mammal. The compounds of the present invention are useful as inhibitors of thrombus formation.

Thus, in one aspect, the present invention is directed to methods for preventing or treating a condition in mammals characterized by abnormal thrombus formation. The pharmaceutically effective amount of the compound or composition of the present invention required as a dose will depend on the route of administration, the type of mammal being treated, and the physical characteristics of the specific mammal under consideration. The dose can be tailored to achieve optimal efficacy but will depend on such factors as weight, diet, concurrent medication and other factors which those skilled in the medical arts will recognize.

In practicing the methods of the invention, the compounds or compositions of the present invention can be used alone or in combination with one another, or in combination with other therapeutic or diagnostic agents. These compounds can be used in vivo, ordinarily in a mammal, preferably in a human, or in vitro. In employing them in vivo, the compounds or compositions can be administered to the mammal in a variety of ways, including parenterally, intravenously, subcutaneously, intramuscularly, colonically, rectally, nasally or intraperitoneally, employing a variety of dosage forms.

In another aspect the present invention is directed to pharmaceutical compositions prepared for storage and subsequent administration which comprise a therapeutically effective amount of a compound of formula I or its pharmaceutically acceptable salt in a pharmaceutically acceptable carrier or diluent.

The therapeutically effective amount of compound of formula I or its pharmaceutically acceptable salt which will be required as a dose will depend on factors which include the route of administration, the type of mammal being treated, and the physical characteristics of the specific mammal under consideration. One skilled in the medical art will appreciate that each composition of therapeutic drug has individual characteristics relating to drug absorption which may affect the amount to be compounded into a given pharmaceutically acceptable carrier or diluent for a therapeutically effective dose. Ansel, H., "Dosage Forms and Routes of Administration", *Introduction to Pharmaceutical Dosage Forms*, 4th Edition, pp. 49–62, Lea & Febiger, Philadelphia (1985).

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, will be within the ambit of one skilled in the art. Typically, applications of compound are commenced at lower dosage levels, with dosage level being increased until the desired effect is achieved.

The dosage for the compounds of the present invention, their pharmaceutically acceptable salts when compounded into pharmaceutically acceptable carriers or diluents can range broadly depending upon the desired affects and the therapeutic indication. Typically, dosages will be between about 0.01 mg/kg and 100 mg/kg body weight, preferably between about 0.01 mg/kg and 10 mg/kg body weight. Administration is preferably parenteral, such as intravenous on a daily basis.

The compounds of formula I may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxilliary substances, such as wetting agents, pH buffering agents, and the like. Ansel, H., *Introduction to Pharmaceutical Dosage Forms*, 4th Edition, pp. 117–358, Lea & Febiger, Philadelphia (1985). Also, if desired, absorption enhancing preparations (e.g., liposomes) may be utilized.

Acceptable carriers or diluents for therapeutic use are well known in the pharmaceutical art, and are described, for example, in *Remington's Pharmaceutical Sciences*, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be included. Id.

To assist in understanding the present invention, the following examples are included which describe the results of a series of experiments. The following examples relating to this invention should not, of course, be construed as specifically limiting the invention. Variations of the invention, now known or later developed, which would be within the purview of one skilled in the art are considered to fall within the scope of the invention as described herein and hereinafter claimed.

The first twenty-nine examples illustrate the preparation of the compounds of the present invention according to the synthetic scheme depicted in FIG. 1. Example A illustrates the use of the compounds of the present invention as an inhibitor of thrombin. Example B illustrates the use of the compounds of the present invention in mammals as an antithrombotic agent.

EXAMPLES

Example 1

Preparation of Alpha-N-t-butoxycarbonyl-N$^g$-nitroargininal

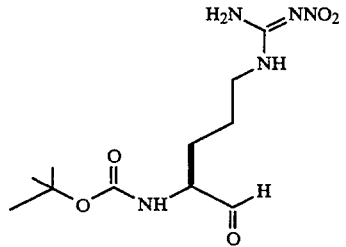

[11]

The following procedure for the synthesis of alpha-t-butoxycarbonyl-N$^g$-nitro-argininal (Compound of Example 1) is a modification of the procedure of Fehrentz, J. A. and Castro, B., Synthesis, 676 (1983).

BOC-N$^g$-nitroarginine was obtained from Calbiochem. N-methylpiperidine, N,O-dimethylhydroxylamine hydrochloride, isobutylchloroformate, and lithium aluminum hydride were obtained from Aldrich Chemical Company, Inc. Dichloromethane, ethyl acetate, methanol, and tetrahydrofuran were obtained from Fisher Scientific Company.

11.4 mL of N-methylpiperidine was slowly added to a stirred suspension of 9.17 g (94 mmole) of N,O-dimethylhydroxylamine hydrochloride in 75 mL of dichloromethane which had been cooled to about 0° C. The solution was allowed to stir for 20 minutes and was kept cold for use in the next step.

In a separate flask, 30.0 g (94 mmole) of Boc-N$^g$-nitroarginine was dissolved by heating in about 1400 mL of tetrahydrofuran and cooled under nitrogen to 0° C. 11.4 mL of N-methylpiperidine and 12.14 mL (94 mmole) of isobutylchloroformate were added and the mixture was stirred for 10 minutes. The free hydroxylamine solution prepared above was added in one portion and the reaction mixture was allowed stir overnight at room temperature.

The resulting precipitate was removed by filtration and washed with 200 mL of tetrahydrofuran. After concentrating the filtrates to about 150 mL under vacuum, 200 mL of ethyl acetate was added, followed by ice to cool the solution. The cooled solution was washed with two 75 mL portions of 0.2 N hydrochloric acid, two 75 mL portions of 0.5 N sodium hydroxide, one 75 mL portion of brine, then was dried with anhydrous magnesium sulfate. Upon concentration under vacuum, 22.7 g (70% yield) of solid BOC-N$^g$-nitroarginine N-methyl-0-methylcarboxamide was isolated. Thin layer chromatographic analysis in 9:1 dichloromethane/methanol (silica gel) showed one spot.

A flask was placed under a nitrogen atmosphere and cooled to −50° C., then was charged with 70 mL (70 mmole) of 1 M lithium aluminum hydride (in tetrahydrofuran) and 500 mL of dry tetrahydrofuran. A solution containing 66 mmole of BOC-N$^g$-nitroarginine N-methyl-O-methylcarboxamide in 50 mL of dry tetrahydrofuran was slowly added while the temperature of the reaction mixture was maintained at −50° C. After allowing the reaction mixture to warm to 0° C. by removal of the cooling bath, it was cooled to −30° C., at which temperature, 100 mL (0.2 mole) of 2N potassium bisulfate was added with stirring, over a 10 to 15 minute period. The reaction mixture was then allowed to stir at room temperature for 2 hours. After removal of the precipitate by filtration, the filtrate was concentrated to 100 mL under vacuum. The concentrate was combined with 200 mL ethyl acetate, then washed with two 50 mL portions of 1N hydrochloric acid, two 50 mL portions of saturated sodium bicarbonate, one 50 mL portion of brine, then was dried over anhydrous magnesium sulfate. The mixture was concentrated under vacuum to yield 13.6 g (70%) of the title compound.

Example 2

Preparation of
N-(Nitroguanidine-1-(S)-(cyanohydroxymethyl)butyl)-1-(1,1-dimethylethoxy)methanamide

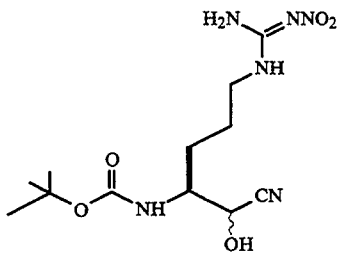 [12]

A solution of 25.2 g (83.1 mmoles) of alpha-Boc-N$^g$-nitro-argininal (the compound of Example 1) in 680 mL tetrahydrofuran was added to a solution of 136 g (1.36 moles) of potassium bicarbonate and 27.6 g (423 mmoles) of potassium cyanide in 680 mL of water. This two phase mixture was allowed to stir vigorously for thirty minutes. The stirring was discontinued and the phases were separated. The aqueous phase was extracted three times with 500 mL ethyl acetate. The tetrahydrofuran phase was diluted with 1000 mL of ethyl acetate. The organic phases were combined and extracted successively with water and brine. This solution was dried over anhydrous magnesium sulfate and concentrated under vacuum to give 28.1 g of the above-identified product as a white foam. This material can be purified by flash chromatography (0 to 6% methanol in dichloromethane) or carried through the next steps directly.

$^1$H NMR(CD$_3$OD) δ1.37 (s, 9H), 1.53 (m, 2H), 1.7 (m, 2H), 3.19 (m, 2H), 3.65 (m, 1H), 4.29 (d, J=7 Hz, 0.35H), 4.48 (d, J=4 Hz, 0.65H).

Example 3

Preparation of
6-Nitroguanidino-3-(S)-(1,1-dimethylethoxy)methanamido-2-hydroxyhexanoic acid methyl ester

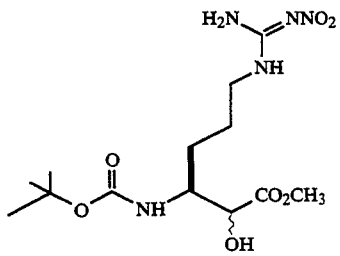 [13]

The 26.0 g (~83 mmole) crude cyanohydrin (compound of the Example 2) was dissolved in 450 mL dioxane, and 450 mL concentrated aqueous hydrochloric acid was slowly added with stirring. This addition was accompanied by vigorous gas evolution. This solution was heated to reflux and stirred for 15 hours. After this period of time, the reaction was allowed to cool to room temperature and then concentrated under vacuum to a thick brown syrup of 6-nitroguanidino-3-(S)-amino-2-hydroxyhexanoic acid hydrochloride salt (compound 3 of FIG. 1).

Crude amino acid 3 (of FIG. 1) from above was concentrated several times from methanol under vacuum and then dissolved in 750 mL of saturated anhydrous hydrochloric acid in methanol. This suspension was refluxed for three hours, allowed to cool to room temperature and concentrated under vacuum. This gave crude 6-nitroguanidino-3-(S)-amino-2-hydroxyhexanoic acid methyl ester hydrochloride salt (compound 4 of FIG. 1) as a thick brown syrup. This was used directly in the next step.

The amino ester (compound 4 of FIG. 1) from above was dissolved in a mixture of 300 mL of saturated sodium bicarbonate and 300 mL tetrahydrofuran. This mixture was treated with di-t-butyldicarbonate (30 g, 137 mmoles) and allowed to stir vigorously for 16 hours. The resulting mixture was extracted with ethyl acetate (1000 mL). The organic layer was washed successively with water then brine, dried over anhydrous magnesium sulfate and concentrated to a small volume under vacuum. The product was purified by flash chromatography (0 to 10% methanol/dichloromethane) to give 13.5 g (49% yield) of the above-identified product as an off-white foam. $^1$H NMR (CDCl$_3$) δ1.41 and 1.45 (s, 9H), 1.7 (m, 4H), 3.2 (m, 2H), 3.82 and 3.84 (s, 3H), 4.10 (m, 1H), 4.19 (bs, 0.65H), 4.33 (bs, 0.35H), 5.02 (d, J=10 Hz, 1H), 5.17 (d, J=10 Hz, 1H).

Example 4

Preparation of
6-Nitroguanidino-3-(S)-(1,1-dimethylethoxy)methanamido-2-hydroxyhexonic acid

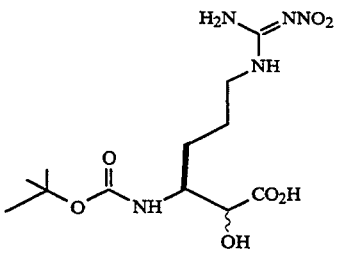 [14]

A solution of the compound of Example 3 (5.0 g, 13.8 mmole) in 100 mL of methanol was treated with 17 mL of 1M lithium hydroxide. This solution was allowed to stir overnight and then treated with 20 mL of Dowex-50 resin X8 400 (H$^+$ form) in 50 mL of deionized water. This solution was swirled for 15 minutes then passed through a 4×4 cm. column of the same resin, the column was washed with 1:1 methanol:water and the combined filtrates were concentrated to dryness under vacuum. The residue was dissolved in 100 mL acetonitrile and concentrated to dryness, this process was repeated two more times to give 4.2 g (87% yield) of the above-identified compound as an off-white foam. $^1$H NMR (CD$_3$OD) δ1.42 and 1.42 (s, 9H), 1.7 (m, 4H), 3.3 (m, 2H), 3.95 (m, 1H), 4.19 (bs, 0.65H), 4.33 (bs, 0.35H), 4.15 (d, J=1 Hz, 0.65H), 4.38 (d, J=4 Hz).

Example 5

Preparation of

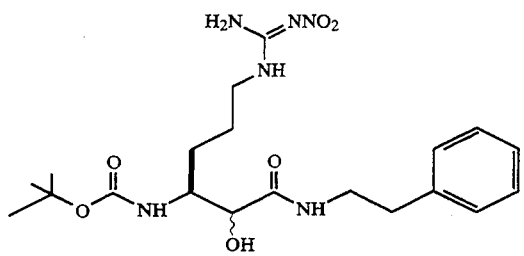 [15]

A 1.05 g portion (2.90 mmole) of the compound of Example 3 was dissolved with stirring in 29 mL of methanol. To this solution was added 3.6 mL of 1N aqueous sodium hydroxide. After 18 hours, thin layer chromatographic analysis (10% methanol/dichloromethane) showed no more starting material. The reaction was neutralized with 1.1 mL of 1N aqueous hydrochloric acid and concentrated under vacuum to dryness. The resulting solid was then dissolved in 15 mL of dimethylformamide with stirring. This solution was treated successively with 0.364 mL (2.90 mmole) 2-phenylethylamine, 0.86 mL (7.83 mmole) 4-methylmorpholine and 1.41 g (3.19 mmole) BOP. After 18 hours, thin layer chromatographic analysis (10% methanol/dichloromethane) showed no more material corresponding to the acid. The reaction mixture was poured into ethyl acetate (300 mL) and washed successively with 1N aqueous hydrochloric acid (75 mL), water (75 mL), saturated sodium bicarbonate (75 mL) and brine (75 mL). The organic layer was dried over anhydrous magnesium sulfate and concentrated under vacuum to a foam. Flash chromatography (silica, 10% methanol/dichloromethane) afforded 1.18 g (90%) of a foam. $R_f=0.33$ (two spots, 10% methanol/dichloromethane).

Example 6

Preparation of

To a solution of the compound of Example 5 (0.675 g, 1.49 mmole) in 17 mL dichloromethane was added 17 mL of trifluoroacetic acid with stirring. After 30 minutes, thin layer chromatographic analysis (10% methanol/dichloromethane) showed no starting material. The trifluoroacetate salt was precipitated by adding 200 mL of diethyl ether and cooled in the freezer for 3 hours. The solid was removed by filtration and rinsed with 75 mL diethyl ether. The resulting solid was dissolved in 7 mL of dimethylformamide with stirring and this solution was treated with 0.627 g (1.49 mmole) α-N-(t-butoxycarbonyl)-L-aspartyl-(β-benzyl ester)-L-proline (the compound of Example 24), 0.44 mL (4.02 mmole) 4-methylmorpholine and 0.72 g (1.64 mmole) BOP. After 18 hours, thin layer chromatographic analysis (10% methanol/dichloromethane) showed no more trifluoroacetate salt. The mixture was added to 300 mL of ethyl acetate and washed successively with 75 mL of 1N aqueous hydrochloric acid, 75 mL of water, 75 mL of saturated sodium bicarbonate and 75 mL of brine. The organic layer was dried over anhydrous magnesium sulfate and concentrated under vacuum. Flash chromatography (silica, 3:1:9 hexane/methanol/dichloromethane) afforded 0.891 g (79%) of a foam. $R_f=0.29$ (10% methanol/dichloromethane).

Example 7

Preparation of

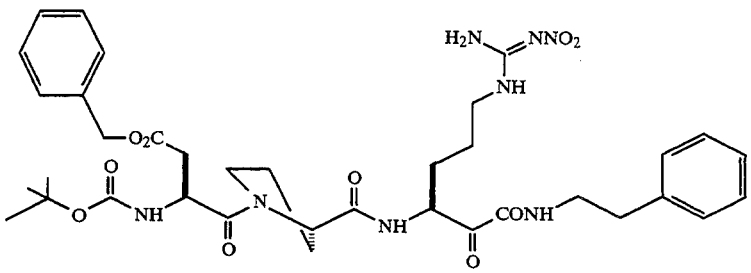 [16]

A 1.0 g portion (1.32 mmole) of the compound of Example 6 was dissolved in 13 mL of dimethylsulfoxide with stirring. This solution was treated with 13 mL of toluene and 2.53 g (13.23 mmole) of ethyl-3-(3-dimethylamino)propylcarbodiimide hydrochloride followed by 0.43 mL (5.29 mmole) of dichloroacetic acid. After 1 hour, thin layer chromatographic analysis (10% methanol/dichloromethane) showed a new spot and no starting material. The mixture was added to 500 mL of ethyl acetate and washed with two 200 mL portions of water and 150 mL of brine. The organic layer was dried over anhydrous magnesium sulfate and concentrated under vacuum. Flash chromatography (silica, 4:1:4 hexane/methanol/dichloromethane) afforded 0.832 g

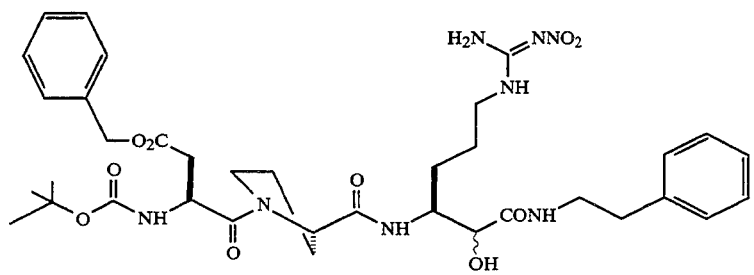 [8]

(83%) of the above-identified compound as a foam. R*f*=0.32 (10% methanol/dichloromethane).

Example 8

Preparation of

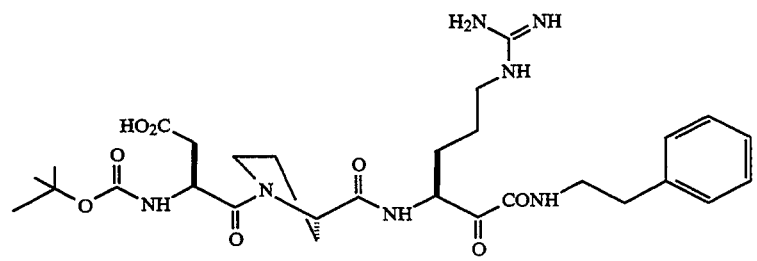

[3]

A 0.512 g portion (0.667 mole) of the compound of Example 7 was dissolved in 50 mL of methanol. This solution was added to a Parr vessel containing 0.5 g 10% Pd/C, followed by 1.32 mL (1.32 mole) 1N aqueous hydrochloric acid. The mixture was shaken under a 10 psig hydrogen atmosphere for 1.5 hours, after which HPLC (reverse phase, 1 mL/minute, 40–80% acetonitrile/water with 0.1% trifluoroacetic acid, 20 minute program, retention time=6.09 minute) showed complete reaction. The mixture was filtered, rinsed with 10 mL of methanol and concentrated under vacuum. The resulting foam was purified by preparative HPLC (reverse phase, 50 mL/minute, 20–60% acetonitrile/water with 0.1% trifluoroacetic acid, 40 minute program). The appropriate fractions were combined and the acetonitrile was removed under vacuum. The remaining liquid was frozen and lyophilized to afford 0.25 g (36%) of the above-identified compound a white fluffy powder. Mass spectral analysis showed the expected molecular ion at 617.3 (calc. 617.3).

ature. After 40 minutes, thin layer chromatographic analysis (10% methanol/dichloromethane) showed no starting material. The trifluoroacetate salt was precipitated by adding 200 mL diethyl ether. The mixture was allowed to cool in the freezer for 3 hours. The solid was removed by filtration, rinsed with 75 mL of diethyl ether, dissolved in 4 mL of dimethylformamide with stirring, and 0.062 mL (0.749 mmole) of 4-methylvaleric acid and 0.2 mL (2.02 mmole) of 4-methylmorpholine were added, followed by 0.36 g of (0.82 mmole) of BOP. After 18 hours, thin layer chromatographic analysis (10% methanol/dichloromethane) showed no more trifluoroacetate salt. The mixture was added to 300 mL of ethyl acetate and washed successively with 100 mL of 1N aqueous hydrochloric acid, 100 mL of water, 100 mL of saturated sodium bicarbonate and 100 mL of brine. The organic layer was dried over anhydrous magnesium sulfate and concentrated under vacuum to a foam. Flash chromatography (silica, 3:1:9 hexane/methanol/dichloromethane) afforded 0.317 g (56%) of the above compound as a foam. R*f*=0.32 (two spots, 10% methanol/dichloromethane).

Example 10

Preparation of

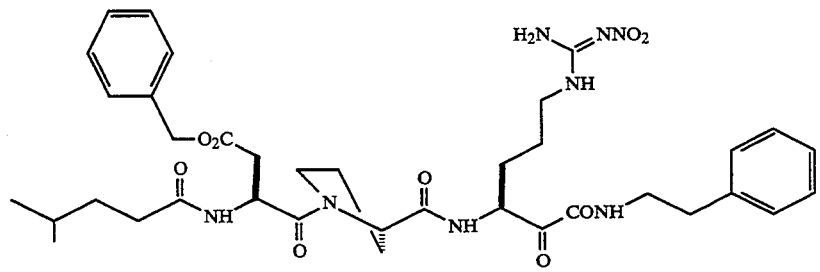

[17]

Example 9

Preparation of

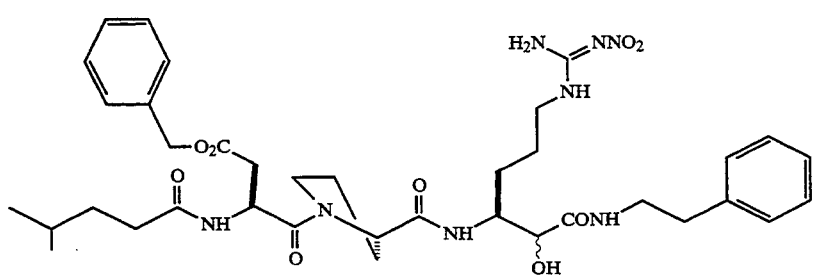

[7]

A 0.236 g portion of the compound of Example 9 (0.313 mmole) was oxidized and worked up as described in Example 7. Flash chromatography (silica, 3:1:9 hex- A solution of the compound of Example 6 (0.566 g, 0.749 mmole) in 14 mL of dichloromethane and 14 mL trifluoroacetic acid was allowed to stir at room temperane/methanol/dichloromethane) of the concentrated organic layer afforded 0.206 g (88%) of the above-iden-

Example 11

Preparation of

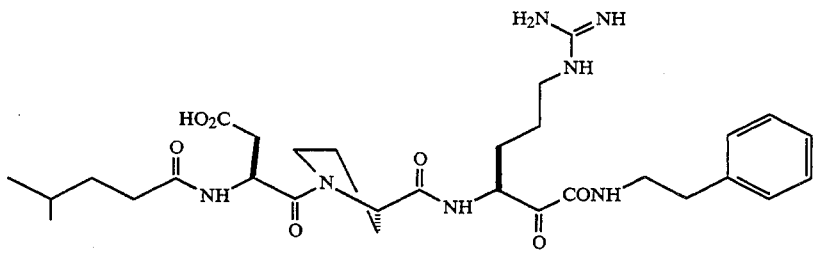

A 0.144 g portion of the compound of Example 10 (0.192 mmole) was hydrogenated and worked up as described in Example 8. The concentrate was purified by preparative HPLC (reverse phase, 50 mL/minute, 20–80% acetonitrile/water with 0.1% trifluoroacetic acid, 40 minute program). The appropriate fractions were combined and the acetonitrile was removed under vacuum. The remaining liquid was frozen and lyophilized to afford 0.57 g (57%) the above-identified compound as a white fluffy powder. Mass spectral analysis showed the expected molecular ion at 615.3 (calc. 615.3).

Example 12

Preparation of

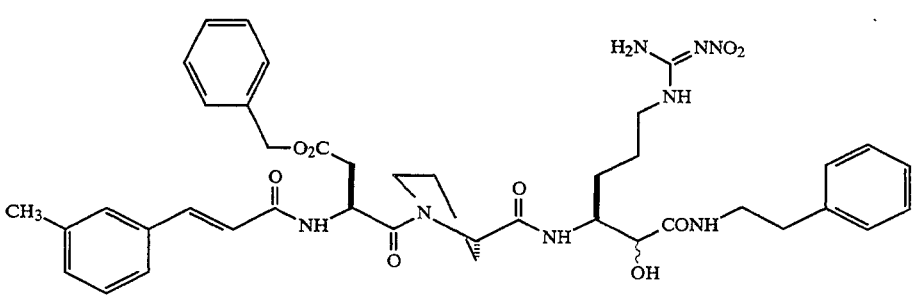

The compound of Example 6 (0.68 g, 1.23 mmole) was converted to the above-identified product using procedures as described in Example 9, using 3-methylcinnamic acid (in place of 4-methyl valeric acid). Flash chromatography (silica, 10% methanol/dichloromethane) afforded 0.582 g (59%) of the above-identified compound as a foam. $R_f$=0.34 (10% methanol/dichloromethane).

Example 13

Preparation of

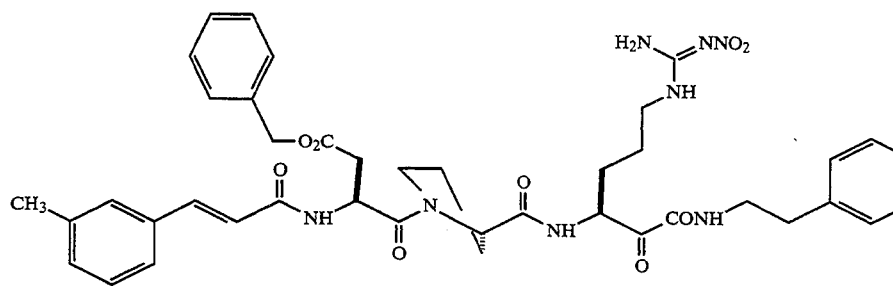

A 0.541 g portion of the compound of Example 12 (0.541 g, 0.675 mmole) was oxidized and worked up as described in Example 7. Flash chromatography (silica, 4:1:4 hexane/methanol/dichloromethane) afforded 0.462 g (85%) of the above-identified compound as a foam. $R_f$=0.37 (10% methanol/dichloromethane).

Example 14

Preparation of

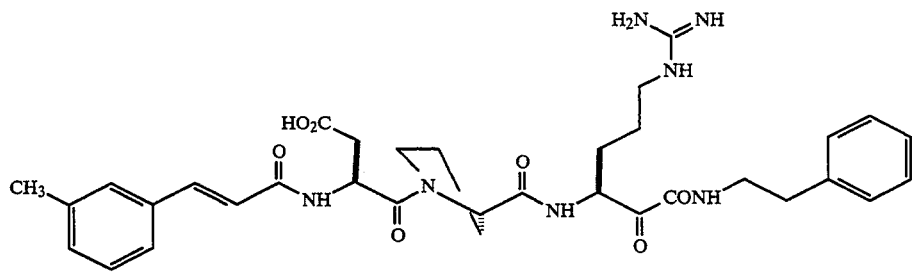

[20]

A 0.109 g portion of the compound of Example 13 (0.136 mmole) was transferred to an hydrofluoric acid reaction vessel. Anisole (0.1 mL) and a stir bar were added. The vessel was flushed with nitrogen and hydrofluoric acid and cooled to −20° C. Hydrofluoric acid (3.0 mL) was distilled into the reaction vessel with stirring. After 30 minutes, the vessel was warmed to 0° C. and flushed with nitrogen. After 1 hour, the hydrofluoric acid was evaporated. The resulting material was extracted with water then 20% acetic acid/water. Both aqueous layers were washed with diethyl ether, frozen and lyophilized. The water extract afforded 10 mg of material and the acetic acid extract afforded 43 mg (58% total). The two fractions were combined and purified by preparative HPLC (reverse phase, 50 mL/minute, 10–60% acetonitrile/water with 0.1% trifluoracetic acid, 40 minute program). Acetonitrile was removed under vacuum from the appropriate fraction. The remaining liquid was frozen and lyophilized to afford the above-identified compound as a white fluffy powder. Mass spectral analysis showed the expected molecular ion at 661.3 (calc. 661.3).

Example 15

Preparation of

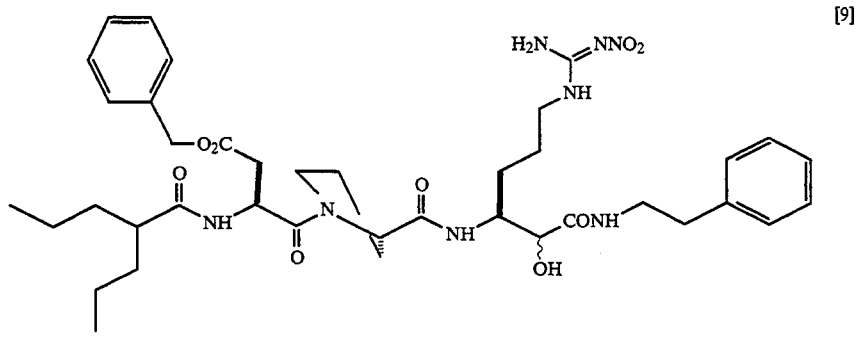

[9]

A 0.637 g portion of the compound of Example 6 (1.15 mmole) was converted to the above-identified product using the methods described in Example 9 and using 2-propylpentanoic acid (in place of 4-methylvaleric acid). Flash chromatography (silica, 10% methanol/dichloromethane) afforded 0.547 g (60%) of the above-identified compound as a foam. $R_f=0.33$ (10% methanol/dichloromethane).

Example 16

Preparation of

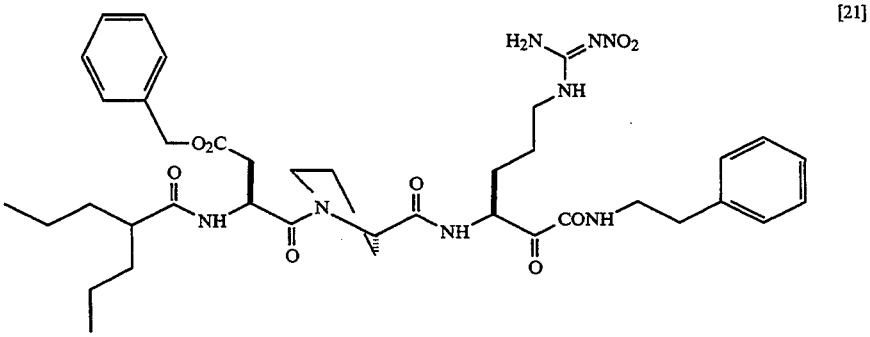

[21]

A 0.505 g portion of the compound of Example 15 (0.646 mmole) was oxidized and worked up as described in Example 7. Flash chromatography (silica, 4:1:4 hexane/methanol/dichloromethane) afforded 0.467 g (95%) of the above-identified compound as a foam. $R_f=0.38$ (10% methanol/dichloromethane).

Example 17

Preparation of

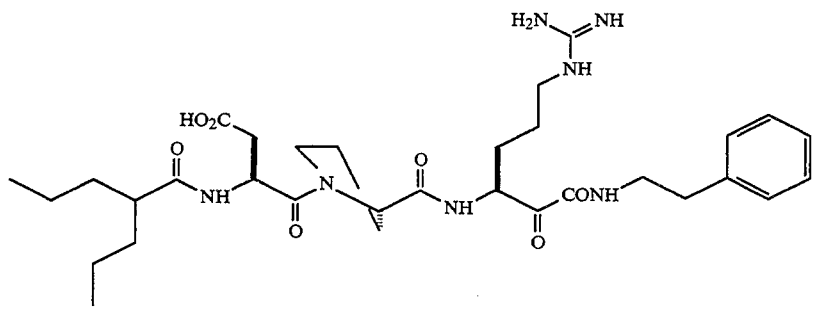

[4]

A 0.105 g portion of the compound of Example 16 (0.134 mmole) was deprotected using hydrofluoric acid as described in Example 15 to afford 30 mg (43%) of material. This material was purified by preparative HPLC (reverse phase, 50 mL/minute, 10-50% acetonitrile/water with 0.1% trifluoroacetic acid, 40 minute program). Acetonitrile was removed under vacuum from the appropriate fraction. The remaining liquid was frozen and lyophilized to afford the above-identified compound as a white fluffy powder. Mass spectral analysis showed the desired ion at 643.3 (calc. 643.4).

Example 18

Preparation of

A 0.89 g portion of the compound of Example 3 (2.45 mmole) was converted to the amide as described in Example 5, using 3-phenylpropylamine (in place of 2-phenylethylamine). Flash chromatography (silica, 4:1:4 hexane/methanol/dichloromethane) afforded 1.03 g (90%) of the above-identified compound as a foam.

Example 19

Preparation of

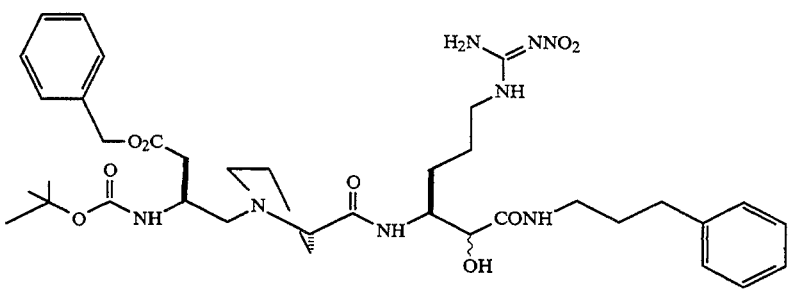

[10]

A 0.5 g portion of the compound of Example 18 (1.07 mmole) was converted to the above product as described in Example 6. Flash chromatography (silica, 10% methanol/dichloromethane) afforded 0.735 g (89%) of the above-identified compound as a foam. $R_f$=0.27 (10% methanol/dichloromethane).

Example 20

Preparation of

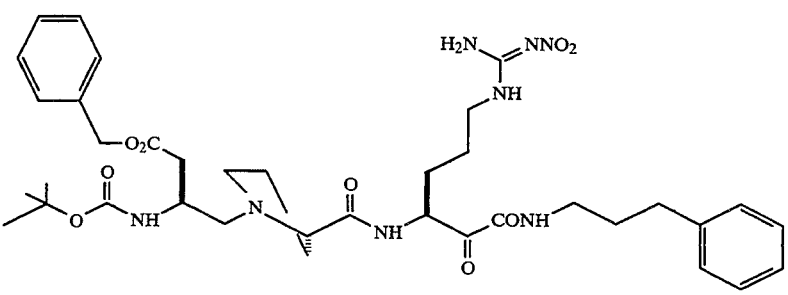

[23]

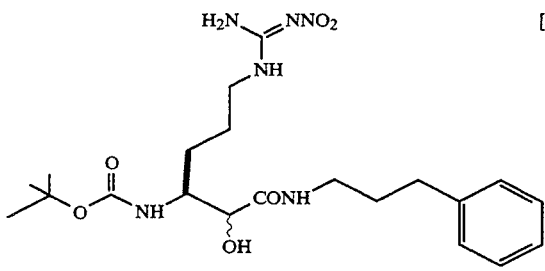

[22]

A 0.70 g portion of the compound of Example 19 (0.909 mmole) was oxidized and worked up as described in Example 7. Flash chromatography (silica, 4:1:4 hexane/methanol/dichloromethane) afforded 0.612 g (87%) of the above-identified compound as a foam. $R_f$=0.41 (10% methanol/dichloromethane).

Example 21

Preparation of

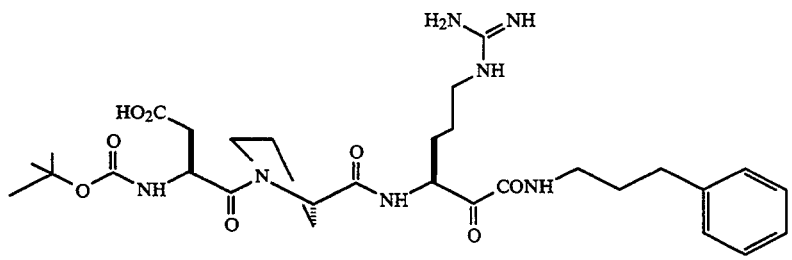

A 0.512 g portion of the compound of Example 20 (0.667 mmole) was hydrogenated and worked up as described in Example 8. The resulting foam was purified by preparative HPLC (reverse phase, 50 mL/minute, 20–60% acetonitrile/water with 0.1% trifluoroacetic acid, 40 minute program) The appropriate fractions were combined, the acetonitrile was removed under vacuum. The remaining liquid was frozen and lyophilized to afford 0.177 g (42%) of the above-identified compound as a white fluffy powder. Mass spectral analysis showed the expected molecular ion at 631.3 (calc. 631.3).

Example 22

Preparation of L-proline-9-fluorenemethyl ester p-toluenesulfonic acid salt

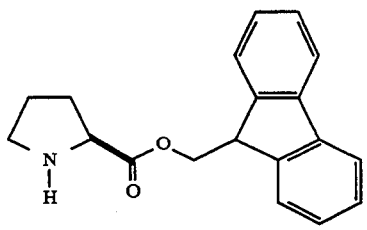

A solution of L-proline (15.99 g, 139.0 mmole), 9-fluorenemethanol (30.0 g, 152.9 mmole), and p-toluenesulfonic acid in 600 mL of toluene was refluxed and water was removed with a Dean-Stark trap. After 26 hours, the reaction was concentrated to give 64 g (99% crude yield) of the above-identified compound as an oil which was used directly in the next step.

Example 23

Preparation of α-N-(t-butoxycarbonyl)-L-aspartyl-(β-benzyl ester)-L-proline-9-fluorenemethyl ester

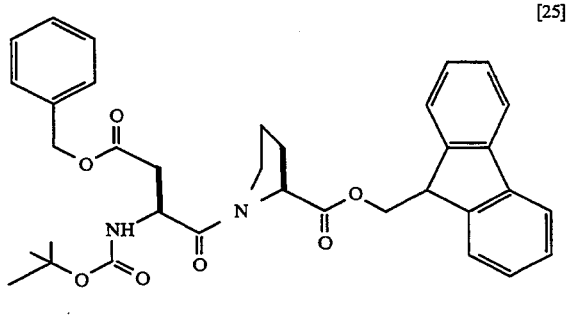

A solution of L-proline-9-fluorenemethyl ester p-toluenesulfonic acid salt (the product of Example 22) (15.44 g, 33.2 mmole), α-N-(t-butoxycarbonyl)-L-aspartic acid-(β-benzyl ester) (9.35 g, 41.9 mmole), benzotriazol-1-yloxy-tris-)dimethylamino)-phosponium-hexafluorophosphate (18.6 g, 42.0 mmole) in 100 mL dimethylformamide was allowed to stir in an ice-bath. This solution was treated with 1-hydroxybenzotriazole hydrate (0.45 g, 3.34 mmole), diisopropylethylamine (19.0 mL, 198 mmole) and the reaction allowed to stir at about 0° to 5° C. for 1.5 hours. After this time the reaction mix was poured into 600 mL of ethyl acetate and extracted successively with saturated aqueous citric acid, water, saturated sodium bicarbonate, and finally brine. The organic phase was dried with anhydrous magnesium sulfate and concentrated under vacuum to give 18 g (91% crude yield) of an oil, which was used directly in the next step.

Example 24

Preparation of α-N-(t-butoxycarbonyl)-L-aspartyl-(β-benzyl ester)-L-proline

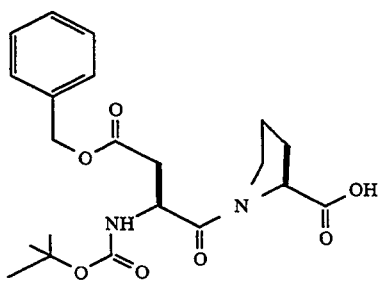

The crude oil from Example 23, α-N-(t-butoxycarbonyl)-L-aspartyl-(β-benzyl ester)-L-proline 9-fluorenemethyl ester (17.5 g, 29.2 mmole), was suspended in 250 mL triethylamine and allowed to reflux for 1 hour. This mixture was concentrated to an oil, dissolved in 600 mL of ethyl acetate. The ethyl acetate phase was washed once with a citric acid solution, once with brine, dried with anhydrous magnesium sulfate, and concentrated under vacuum to give an oil. This material was purified by column chromatography (silica gel, 10–20% tetrahydrofuran/dichloromethane) to give 7.5 g (yield about 38% overall) of the above-identified compound.

Example 25

Preparation of

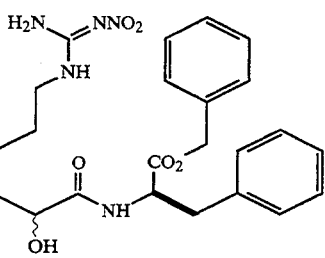
[27]

A solution of 400 mg of the compound of Example 4 (1.14 mmole) was dissolved with stirring into 2 mL of dimethylformamide. This solution was treated successively with D-phenylalanine benzyl ester p-toluenesulfonic acid salt (489 mg, 1.14 mmole), 4-methylmorpholine (0.342 mL, 3.11 mmole) and BOP (5.15 mg, 1.16 mmole). After 2 hours, thin layer chromatographic analysis (10% methanol/dichloromethane) showed no more material corresponding to the acid. The reaction mixture was poured into ethyl acetate (300 mL) and washed successively with 1N aqueous hydrochloric acid (75 mL), water (75 mL), saturated sodium bicarbonate (75 mL) and brine (75 mL). The organic layer was dried over anhydrous magnesium sulfate and concentrated under vacuum. This afforded 600 mg (90%) of the above-identified compound as a white foam. $R_f=0.70$ (two spots, 10% methanol/dichloromethane).

Example 26

Preparation of

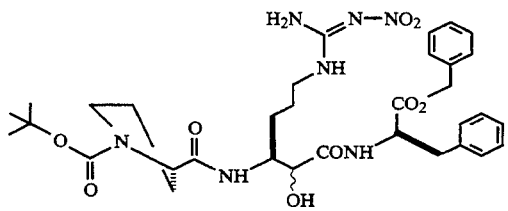
[28]

To a solution of 586 mg of the compound of Example 25 (1.00 mmole) in 17 mL dichloromethane, was added 17 mL of trifluoroacetic acid with stirring. After 30 minutes, thin layer chromatographic analysis (10% methanol/dichloromethane) showed no starting material. The trifluoroacetate salt was isolated by concentrating the solution. The residue was dissolved in toluene and then concentrated to an oil, which had some trifluoroacetic acid. The oil was dissolved in 3 mL of dimethylformamide with stirring and this soltion treated with (264 mg, 1.49 mmole) α-N-t-butoxycarbonyl-L-proline, 0.600 mL (6.7 mmole) 4-methylmorpholine and 554 mg (1.23 mmole) BOP. After 1 hour, thin layer chromatographic analysis (10% methanol/dichloromethane) showed no more trifluoroacetate salt. The mixture was added to 300mL of ethyl acetate and washed successively with 75mL of 1N aqueous hydrochloric acid, 75 mL of water, 75 mL of saturated sodium bicarbonate and 75 mL of brine. The organic layer was dried over anhydrous magnesium sulfate and concentrated under vacuum. This afforded 700 mg of the above-identified compound as a white foam, $R_f=0.70$ (two spots, 10% methanol/dichloromethane).

Example 27

Preparation of

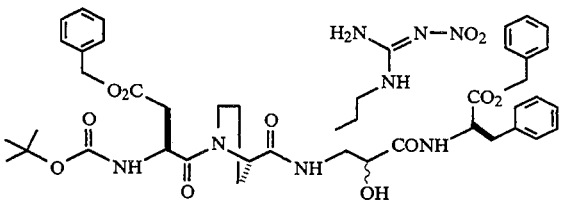

This compound was synthesized by the procedure described in Example 26, except that an equimolar amount of the compound of Example 26 and Boc-L-aspartic acid-β-benzyl ester) was used, instead of (α-N-t-butoxycarbonyl-L-proline. This gave 825 mg of the above-identified compound ($R_f=0.5$, two spots, 10% methanol/dichloromethane).

Example 28

Preparation of

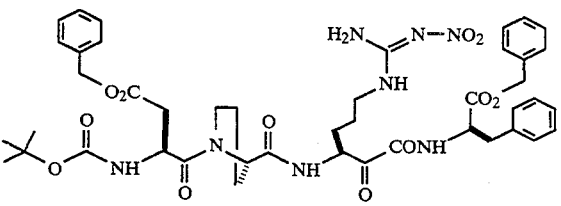

A 370 mg portion of the compound of Example 27 (0.42 mmole) was dissolved in 4 mL of dimethylsulfoxide with stirring. This solution was treated with 4 mL of toluene and 816 mg (4.26 mmole) of ethyl-3-(3-dimethylamino)propylcarbodiimide hydrochloride followed by 0.150 mL of dichloroacetic acid. After 1 hour, thin layer chromatographic analysis (10% methanol/dichloromethane) showed a single new spot and no starting material. The mixture was added to 500mL of ethyl acetate and washed with two 200 mL portions of water and 150 mL of brine. The organic layer was dried over anhydrous magnesium sulfate and concentrated under vacuum. Flash chromatography (silica, 0 to 4% methanol/dichloromethane) afforded 200 mg (54 % yield) of the above-identified compound as a foam. $R_f=0.55$ (10% methanol/dichloromethane).

Example 29

Preparation of

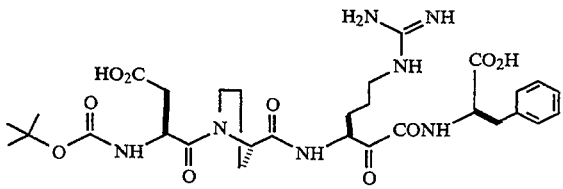

A 0.160 mg portion of the compound of Example 28 (0.180 mmole) was dissolved in 25 mL of methanol. This solution was added to a Parr vessel containing 150 mg 10% Pd/C, followed by 0.20 mL (0.20 mmole) 1N aqueous hydrochloric acid and 0.2 mL of glacial acetic acid. The mixture was shaken under a 10 psig hydrogen atmosphere for 1.5 hours, after which HPLC (reverse phase, 1 mL/minute, 5–95% acetonitrile/water with 0.1% trifluoroacetic acid, 20 minute program, retention time =14.5 minute) showed complete reaction. The mixture was filtered, rinsed with 10 mL of methanol and concentrated under vacuum. The resulting foam was purified by preparative HPLC (reverse phase, 50 mL/minute, 10–60% acetonitrile/water with 0.1% trifluoroacetic acid, 40 minute program). The appropriate fractions were combined and the acetonitrile was removed under vacuum. The remaining liquid was frozen and lyophilized to afford 100 mg of the above-identified compound as a white fluffy powder. Mass spectral analysis showed the expected molecular ion at 661.3 (calc. 661.3 ).

Example A

Thrombin Assay

The ability of the compounds of the present invention to act as inhibitors of thrombin catalytic activity was assessed by determining their inhibition constant, Ki, and the concentration which inhibited enzyme activity by 50%, IC$_{50}$, against thrombin.

Enzyme activity was determined using the chromogenic substrates, S2266 (H-D-valyl-L-leucyl-L-arginine-p-nitroaniline, obtained from Kabi Diagnostica) or Pefachrome t-PA (CH$_3$SO$_2$-D-hexahydrotyrosine-glycyl-L-Arginine-p-nitroaniline, obtained from Pentapharm Ltd.). The subtrates were reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

The assay for Ki determinations was conducted by combining in appropriate wells of a Corning microtiter plate, 50 μL of HBSA, 50 μL of the test compound at a specified concentration diluted in HBSA (or HBSA alone for V$_{o(uninhibited\ velocity)}$ measurement), and 50 μL of the chromogenic substrate S-2266 at a specified concentration diluted in HBSA. At time zero, 50 μL of α-thrombin diluted in HBSA, was added to the wells yielding a final concentration of 0.5 nM in a total volume of 200 μL. Velocities of S-2266 substrate hydrolysis which occurred over a designated time period was measured by the change in absorbance at 405nm using a Thermo Max ® Kinetic Microplate Reader.

Ki values were determined for test compounds using the following methodologies: 1) For test compounds exhibiting slow binding or slow-tight binding kinetics, Ki values were determined using the relationships developed by Williams and Morrison, Methods in Enzymology, 63: 437 (1979) using steady state velocities (Vs) measured over 40 minutes. The extent of substrate hydrolysis was less than 5% over the course of this assay. 2) For test compounds showing rapid, reversible kinetics of inhibition, Ki values were determied from initial velocities using the relationships developed by Dixon, M., Biochem. J., 129: 197 (1972).

IC$_{50}$ determinations were conducted where HBSA (50 μl), α-thrombin (50 μl) and inhibitor (50 μl) (covering a broad concentration range), were combined in appropriate wells and incubated for 30 minutes at room temperature prior to the addition of substrate Pefachrome-t-PA (50 μl ). The initial velocity of Pefachrome t-PA hydrolysis was measured by the change in absorbance at 405nm using a Thermo Max ® Kinetic Microplate Reader over a 5 minute period in which less than 5% of the added substrate was utilized. The concentration of added inhibitor which caused a 50% decrease in the initial rate of hydrolysis was defined as the IC$_{50}$ value.

Table I below gives the Ki and IC$_{50}$ values for selected test compounds. The data shows their utility as potent in vitro inhibitors of human α-thrombin.

TABLE I

| Inhibitor Constants (Ki) and IC$_{50}$'s of Compounds | | |
|---|---|---|
| Compound | Ki (nM) | IC$_{50}$ (nM) |
| 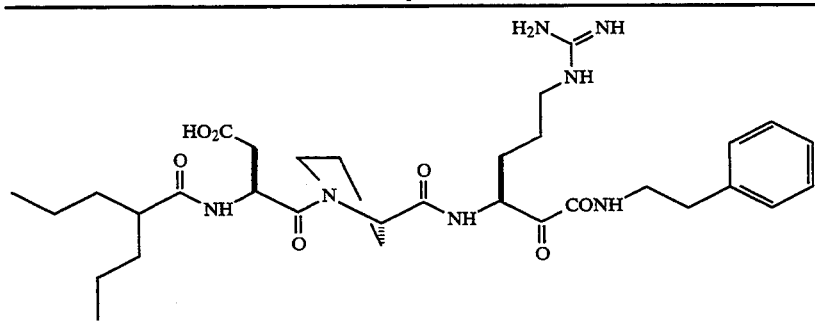 | 1.5 | 0.7 |
| 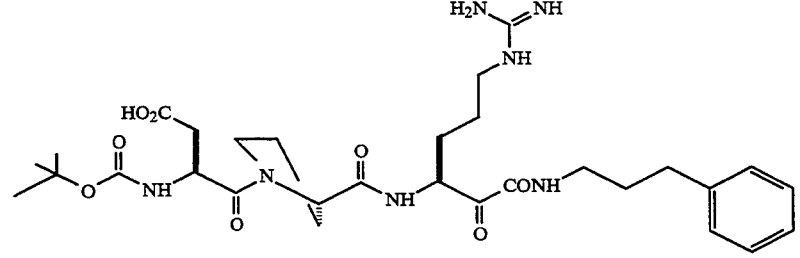 | 5.5 | 6.5 |

TABLE I-continued

Inhibitor Constants (Ki) and IC50's of Compounds

| Compound | Ki (nM) | IC50 (nM) |
|---|---|---|
| 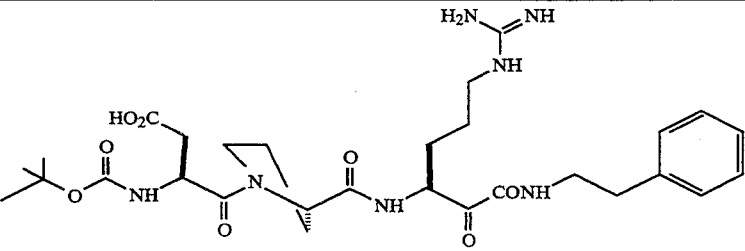 | 11.0 | 2.2 |

Example B
Experimental Models of Thrombosis

The antithrombotic properties of the compound of Example 8 was evaluated using the following established experimental models of acute thrombosis.

Extracorporeal Shunt Model in Rats

This is one of the most common and generally used models in the evaluation of antithrombotic compounds. Smith, J. R. and White, A.M. Br. J. Pharmacol., 77: 29-38 (1982). In this model a localized clot made up of primarily fibrin with some platelet and macrophage involvement (Shand, R. A. and Smith, J. R. and Wallis, R. B. Thromb. Res., 36: 223-232 (1984)), is formed on an artificial thrombogenic surface (typically a segment of silk or cotton thread) contained in a sialstic chamber which is part of an exteriorized shunt between the carotid artery and jugular vein.

The effect of the compound of Example 8 on the formation of a thrombus on the thrombogenic surface was measured using clot weight as the primary end point in the model.

Male Harlan Sprague Dawley rats (420–450 g) were acclimated at least 72 hours prior to use. The animals were fasted for 12 hours prior to surgery with free access to water. The animals were anesthetized with a sodium pentobarbital (Nembutal) given intraperitoneally at a dose of 50 mg/kg body weight and placed on a isothermal pad to maintain body temperature. The level of anesthesia was monitored every 15 minutes by: neuro-response to a tail pinch, respiration and core temperature. The desired depth of surgical anesthesia was maintained by administering subsequent doses (5 mg/kg) intravenously. The left femoral artery was catheterized using standard procedures for blood pressure monitoring and blood sampling, with polyethylene tubing (PE50). The left and right femoral veins were catheterized with PE50 tubing for delivery of anethestic and test compounds, respectively.

Following surgery the animals were randomized in either a control (saline infusion) or treatment group (Compound of Example 8) with at least 6 animals per group per dose. The exteriorized shunt was assembled prior to catheterization by connecting two pieces of saline filled 12.5 cm PE90 tubing with a 6 cm piece of PE160 tubing containing a 6 cm piece of silk suture size 3 and clamped with hemostats. A small 0.5 cm portion of the silk thread protrudes from the junction of the chamber with the shunt. The left jugular vein and right carotid artery were catheterized with the ends of the PE90 shunt. Prior to unclamping the shunt, the test compound (Compound of Example 8) was dissolved in normal saline, and infused via the right femoral vein as an initial bolus (0.5 mg/kg) followed by a continuous intravenous infusion (at the designated doses shown in the following table) for 30 minutes prior to exposure of the suture to flowing blood. Blood pressure, heart rate core temperature and respiration were monitored continuously. At the designated time, blood flow through the chamber was initiated by unclamping the shunt and allowed to flow for a period of 15 minutes during which time the test compound continued to be administered. At the end of the exposure period both sides of the chamber were clamped and the suture containing the clot removed following detachment of the arterial end of the chamber. The clot was immediately weighed and recorded. Following termination of the experiment the animal was euthanized with a 120 mg/kg dose of Nembutal. One experiment was performed per animal.

The efficacy of the compound of Example 8 as an antithrombotic agent in this in vivo model was demonstrated by the reduction in clot size, as shown in Table II below.

TABLE II

| Treatment Group | Clot size (mg)[a] |
|---|---|
| Control | 41.30 ± 3.42 |
| Group 1 | 38.37 ± 4.49 |
| Group 2 | 17.22 ± 1.79* |
| Group 3 | 10.20 ± 0.636* |

Control-no treatment
Group 1-0.5 mg/kg i.v. bolus + 20 μg/kg/min i.v. infusion
Group 2-0.5 mg/kg i.v. bolus + 50 μg/kg/min i.v. infusion
Group 3-0.5 mg/kg i.v. bolus + 100 μg/kg/min i.v. infusion
[a]weights are designated as the mean ± S.E.M. (n = 6).
*p ≦ 0.01 vs Control by one-way ANOVA followed by Newman-Kuels Test.

Rat model of FeCl3-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In contrast to the exteriorized shunt model, thrombus development in this model is relatively heparin insensitive which suggests that this model may be more representative of the type of thrombosis which has been observed clinically in newly re-canalized coronary vessels following balloon angioplasty or enzymatic thrombolysis. In this model a platelet-rich, occlusive thrombus is formed in a segment of the rat carotid artery treated with a fresh solution of FeCl3 absorbed to a piece of filter paper. The FeCl3 is thought to diffuse into the treated segment of artery and causes de-endothelialization resulting in thrombus formation. The effect of a test compound on the incidence of occlusive thrombus formation following the application of the FeCl3 is monitored by ultrasonic flowtometry and is used as the primary end point. The use of flowtometry is a modification of the original procedure in which thermal detection of clot formation was employed. Kurz, K. D., Main, B. W., and Sandusky, G. E., *Thromb. Res.*, 60: 269-280 (1990).

Male Harlan Sprague Dawley rats (420-450 g) were acclimated at least 72 hours prior to use and fasted for 12 hours prior to surgery with free access to water. The animals were prepared, anesthetized with Nembutal with catheters for blood pressure monitoring, drug and anesthesia delivery being implanted as described above. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline infusion) or treatment group with test compound (Compound of Example 8) with at least 6 animals per group per dose. The test compounds were administered as described above after placement of the flow probe and stabilization of the preparation for a period of 30 min prior to the thrombogenic stimulus. At t=0, a 3 mm diameter piece of filter paper (Whatman #3) soaked with 10 μL of a 35% solution of fresh FeCl3 (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point. Following the 60 minute observation period the flow probe was removed and the area cleared of all excess fluid. The distal and proximal sutures were tied off and arterial clamps placed on the far proximal and distal ends of the segment. The isolated segment was cut out, blotted dry on filter paper and weighed. The segment was re-weighed following removal of the clot and the difference recorded as total % clot weight. The animals were euthanized as described above.

The efficacy of the compound of Example 8 as an antithrombotic agent in this in vivo model was demonstrated by the reduction in the incidence of occlusion and in clot size, as shown in Table III below.

TABLE III

Results of the Compound of Example 8 in the FeCl3 Model of Thrombosis in Rats.

| Treatment Group[a] | Incidence of Occlusion[b] | Clot Size[c] |
|---|---|---|
| Control | 6/6 | 68.65 ± 3.75 |
| Group 1 | 5/6 | 40.73 ± 8.0*** |
| Group 2 | 1/6* | 12.56 ± 5.96*** |
| Group 3 | 0/6** | 4.46 ± 3.49*** |

[a]Control-no treatment
Group 1-0.5 mg/kg i.v. bolus + 20 μg/kg/min i.v. infusion
Group 2-0.5 mg/kg/i.v. bolus + 50 μg/kg/min i.v. infusion
Group 3-0.5 mg/kg i.v. bolus + 100 μg/kg/min i.v. infusion
[b]Occlusion is defined as the establishment of zero blood flow through the treated segment of the carotid artery.
[c]Clot size is defined as: [Isolated clot/(Intact segment-Empty segment)] × 100. Numbers represent the mean ± S.E.M. (n = 6).
*$p \leq 0.05$ vs Control by Chi-Square Analysis
**$p \leq 0.005$ vs Control by Chi-Square Analysis
***$p < 0.01$ vs Control by one-way ANOVA followed by Newman-Kuels Test These in vivo data clearly demonstrated the antithrombotic efficacy of the Compound of Example 8 in two well established models of experimental thrombosis.

We claim:
1. A compound having the structure

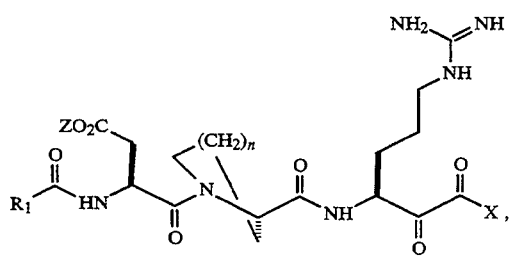

wherein $R_1$ is alkyl of about 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms;

z is hydrogen, alkyl of about 1 to about 12 carbon atoms, alkenyl of about 3 to about 6 carbon atoms, aryl of about 6 to about 14 carbon atoms, aralkyl of about 6 to about 15 carbon atoms, or aralkenyl of about 8 to about 15 carbon atoms;

n is 0, 1, or 2; and

X is —N(R$_2$)—Y—Ar,

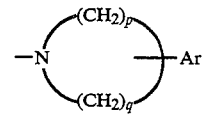

or —NH(R$_6$), wherein $R_2$ is hydrogen, lower alkyl of about 1 to about 4 carbon atoms, or aryl of about 6 to about 14 carbon atoms;

Ar is aryl of about 6 to about 14 carbon atoms which is optionally substituted with 1 or 2 substituents each independently selected from amino, carboxy, carboxamide, fluoro, nitro, trifluoromethyl, lower alkyl of about 1 to about 4 carbon atoms, and lower alkoxy of about 1 to about 4 carbon atoms;

Y is —CH(R$_3$)—, —CH(R$_3$)—CH(R$_4$)—, or —CH(R$_3$)—CH(R$_4$)—CH(R$_5$)—, wherein R$_3$ is hydrogen, carboxy, carboxamide, alkylenehydroxy of about 1 to about 4 carbon atoms, lower alkyl of about 1 to about 4 carbon atoms, alkylenecarboxy of about 2 to about 5 carbon atoms, alkylenecarboxamide of about 2 to about 5 carbon atoms, or aryl of about 6 to about 14 carbon atoms; R$_4$ is hydrogen, lower alkyl of about 1 to about 4 carbon atoms, or aryl of about 6 to about 14 carbon atoms; and R$_5$ is hydrogen, lower alkyl of about 1 to about 4 carbon atoms, or aryl of about 6 to about 14 carbon atoms; provided that no more than one R$_3$, R$_4$, or R$_5$ is aryl of about 6 to about 14 carbon atoms;

p and q are independently selected integers from 1 to 5 and the sum of p+q is 4 to 8; and R6 is naphthyl, 1,2,3,4-tetrahydronaphthyl, (1,2,3,4-tetrahydronaphthyl)methylene, or indanyl, and pharmaceutically acceptable salts thereof.

2. A compound of claim 1, wherein Z is hydrogen or indan-5-yl.

3. A compound of claim 2, wherein Z is hydrogen.

4. A compound of claim 3, wherein $R_1$ is a branched alkyl group.

5. A compound of claim 4, wherein $R_1$ is selected from group consisting of 2,2-dimethylethyloxy, 2,2-dimethylpropyl, 3-methylbutyl, and 1-propylbutyl.

6. A compound of claim 5, wherein X is —N($R_2$)—CH($R_3$)—CH($R_4$)—Ar.

7. A compound of claim 6, wherein X is 2-phenylethylamine.

8. A compound of claim 7, wherein n is 1.

9. A compound of claim 5, wherein X is —N($R_2$)—CH($R_3$)—CH($R_4$)—CH($R_5$)—Ar.

10. A compound of claim 9, wherein X is 3-phenylpropylamine.

11. A compound of claim 10, wherein n is 1.

12. A compound of claim 2, wherein Z is indan-5-yl.

13. A compound of claim 12, wherein $R_1$ is a branched alkyl group.

14. A compound of claim 13, wherein $R_1$ is selected from a group consisting of 2,2-dimethylethyloxy, 2,2-dimethylpropyl, 3-methylbutyl, and 1-propylbutyl.

15. A compound of claim 14, wherein X is —N($R_2$)—CH($R_3$)—CH($R_4$)—Ar.

16. A compound of claim 15, wherein X is 2-phenylethylamine.

17. A compound of claim 16, wherein n is 1.

18. A compound of claim 14, wherein X is —N($R_2$)—CH($R_3$)—CH($R_4$)—CH($R_5$)—Ar.

19. A compound of claim 18, wherein X is 3-phenylpropylamine.

20. A compound of claim 19, wherein n is 1.

21. A compound according to claim 1 selected from the group consisting

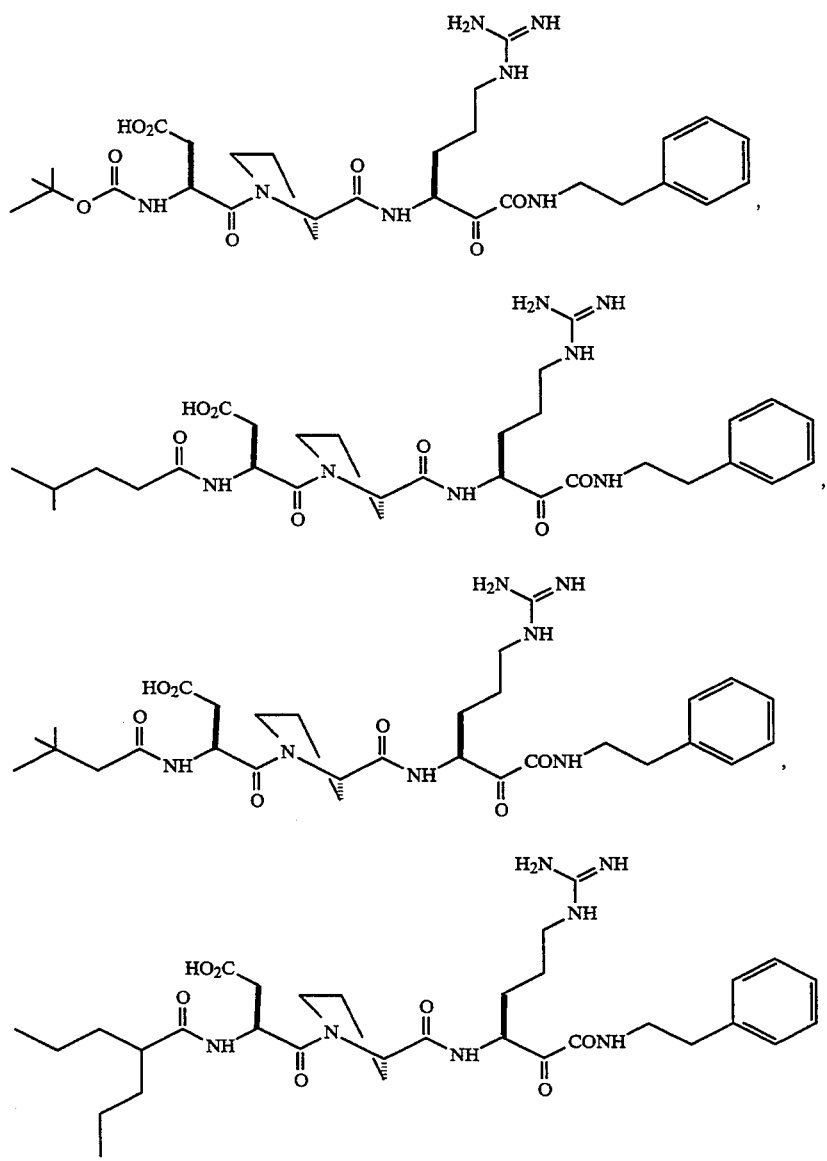

and

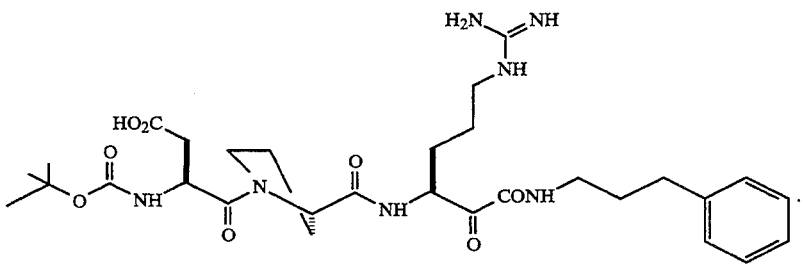

22. A pharmaceutical composition comprising a pharmaceutically acceptable carrier and therapeutically effective amount of the compound of claim 1, 2, 3, 4, 5, 6, 7, 8, 9, 10, 11, 12, 13, 14, 15, 16, 17, 18, 19, 20, or 21.

23. A method for preventing or treating in a mammal a condition of abnormal thrombus formation comprising administering to said mammal a therapeutically effective amount of the compound of claim 1, 2, 3, 4, 5, 6, 7, 8, 9, 10, 11, 12, 13, 14, 15, 16, 17, 18, 19, 20 or 21.

24. A method for preventing or treating in a mammal a condition of abnormal thrombus formation comprising administering to said mammal a therapeutically effective amount of the compound of claim 22.

25. A compound having the structure

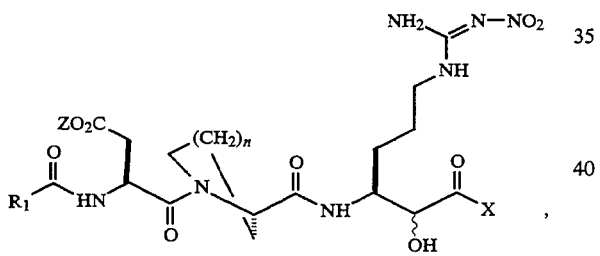

wherein $R_1$ is alkyl of about 1 to about 12 carbon atoms, alkenyl of about 3 to about 6 carbon atoms, aryl of about 6 to about 14 carbon atoms, aralkyl of about 6 to about 15 carbon atoms, aralkenyl of about 8 to 15 carbon atoms, alkoxy of about 1 to about 12 carbon atoms, alkenyloxy of about 3 to about 8 carbon atoms, aryloxy of about 6 to about 14 carbon atoms, or aralkyloxy of about 6 to about 15 carbon atoms;

z is hydrogen, alkyl of about 1 to about 12 carbon atoms, alkenyl of about 3 to about 6 carbon atoms, aryl of about 6 to about 14 carbon atoms, aralkyl of about 6 to about 15 carbon atoms, or aralkenyl of about 8 to about 15 carbon atoms;

n is 0, 1, or 2; and

X is —N($R_2$)—Y—Ar,

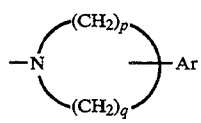

or —NH($R_6$), wherein $R_2$ is hydrogen, lower alkyl of about 1 to about 4 carbon atoms, or aryl of about 6 to about 14 carbon atoms;

Ar is aryl of about 6 to about 14 carbon atoms which is optionally substituted with 1 or 2 substituents each independently selected from a group consisting of amino, carboxy, carboxamide, fluoro, nitro, trifluoromethyl, lower alkyl of about 1 to about 4 carbon atoms, and lower alkoxy of about 1 to about 4 carbon atoms;

Y is —CH($R_3$)—, —CH($R_3$)—CH($R_4$)—, or —CH($R_3$)—CH($R_4$)—CH($R_5$)—, wherein $R_3$ is hydrogen, carboxy, carboxamide, alkylenehydroxy of about 1 to about 4 carbon atoms, lower alkyl of about 1 to about 4 carbon atoms, alkylenecarboxy of about 2 to about 5 carbon atoms, alkylenecarboxamide of about 2 to about 5 carbon atoms, or aryl of about 6 to about 14 carbon atoms; $R_4$ is hydrogen, lower alkyl of about 1 to about 4 carbon atoms, or aryl of about 6 to about 14 carbon atoms; and $R_5$ is hydrogen, lower alkyl of about 1 to about 4 carbon atoms, or aryl of about 6 to about 14 carbon atoms; provided that no more than one $R_3$, $R_4$, or $R_5$ is aryl of about 6 to about 14 carbon atoms;

p and q are independently selected integers from 1 to 5 and the sum of p+q is 4 to 8; and $R_6$ is naphthyl, 1,2,3,4-tetrahydronaphthyl, (1,2,3,4-tetrahydronaphthyl)methylene, or indanyl.

26. A compound of claim 25, wherein Z is benzyl.

27. A compound of claim 26, where in $R_1$ is a branched alkyl group.

28. A compound of claim 27, wherein $R_1$ is selected from a group comprising of 2,2-dimethylethyloxy, 2,2-dimethylpropyl, 3-methylbutyl, and 1-propylbutyl.

29. A compound of claim 28, wherein X is —N($R_2$)—CH($R_3$)—CH($R_4$)—Ar.

30. A compound of claim 29, wherein X is 2-phenylethylamine.

31. A compound of claim 30, wherein n is 1.

32. A compound of claim 28, wherein X is —N($R_2$)—CH($R_3$)—CH($R_4$)—CH($R_5$)—Ar.

33. A compound of claim 32, wherein X is 3-phenylpropylamine.

34. A compound of claim 33, wherein n is 1.

35. A compound of claim 25 selected from the group consisting of

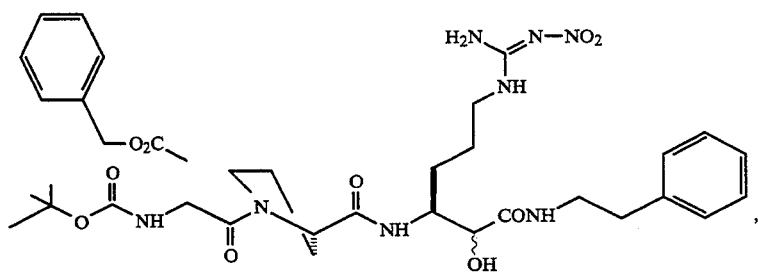
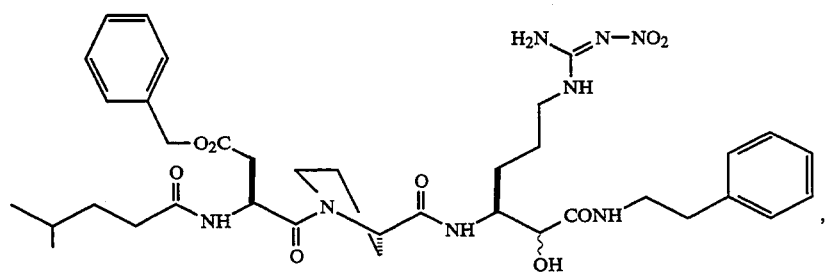
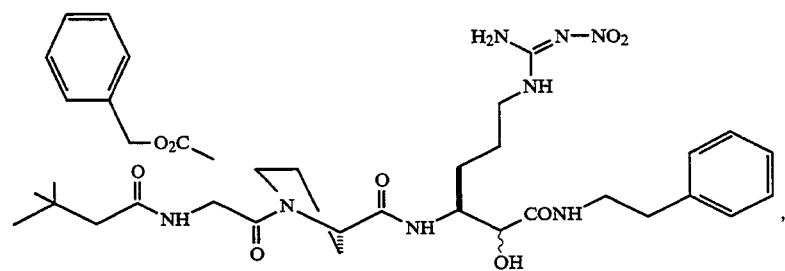
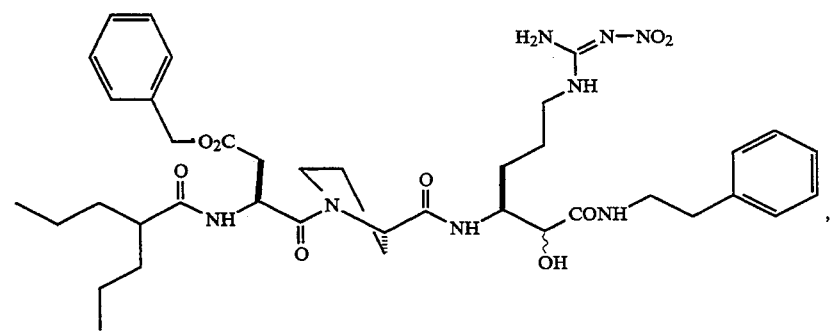
and
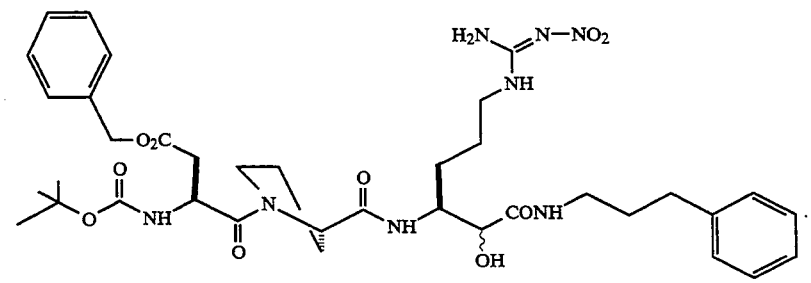
* * * * *